US010206693B2

(12) United States Patent
Piferi

(10) Patent No.: US 10,206,693 B2
(45) Date of Patent: Feb. 19, 2019

(54) MRI-GUIDED MEDICAL INTERVENTIONAL SYSTEMS AND METHODS

(71) Applicant: MRI Interventions, Inc., Memphis, TN (US)

(72) Inventor: Peter Piferi, Orange, CA (US)

(73) Assignee: MRI Interventions, Inc., Irvine, CA (US)

( * ) Notice: Subject to any disclaimer, the term of this patent is extended or adjusted under 35 U.S.C. 154(b) by 583 days.

(21) Appl. No.: 13/781,049

(22) Filed: Feb. 28, 2013

(65) Prior Publication Data

US 2014/0024927 A1   Jan. 23, 2014

Related U.S. Application Data

(60) Provisional application No. 61/673,583, filed on Jul. 19, 2012.

(51) Int. Cl.
| | | |
|---|---|---|
| A61B 17/17 | (2006.01) | |
| A61B 90/11 | (2016.01) | |
| A61B 5/055 | (2006.01) | |

(52) U.S. Cl.
CPC ...... *A61B 17/1703* (2013.01); *A61B 17/1739* (2013.01); *A61B 90/11* (2016.02); *A61B 5/055* (2013.01)

(58) Field of Classification Search
USPC ................................ 600/417, 424, 427, 429
See application file for complete search history.

(56) References Cited

U.S. PATENT DOCUMENTS

| | | | | |
|---|---|---|---|---|
| 5,116,345 A | * | 5/1992 | Jewell | .................. A61B 19/201 606/130 |
| 5,507,742 A | * | 4/1996 | Long et al. | ..................... 606/15 |
| 6,529,765 B1 | | 3/2003 | Franck et al. | |
| 6,675,037 B1 | * | 1/2004 | Tsekos | .......................... 600/417 |

(Continued)

FOREIGN PATENT DOCUMENTS

WO   WO 2012/072112 A1   6/2012

OTHER PUBLICATIONS

Notification of Transmittal of the International Search Report and the Written Opinion of the International Searching Authority, or the Declaration, PCT/US2014/060644, dated Jan. 26, 2015.

(Continued)

*Primary Examiner* — Tse W Chen
*Assistant Examiner* — Joanne M Hoffman
(74) *Attorney, Agent, or Firm* — Myers Bigel, P.A.

(57) ABSTRACT

A trajectory frame for use with an MRI-guided interventional system includes a base having a patient access aperture formed therein. The base is configured to be secured to the body of a patient. A yoke is mounted to the base and is rotatable about a roll axis. A platform is mounted to the yoke and is rotatable about a pitch axis. An elongated guide is secured to the platform and includes opposite proximal and distal end portions and a bore that extends from the proximal end portion to the distal end portion. The guide distal end portion is positioned proximate the patient access aperture. The guide is configured to removably receive various devices therein for quick release therefrom, including a targeting cannula, drill guide and drill bit, skull fixation device and driver, and catheter guide.

15 Claims, 23 Drawing Sheets

(56) References Cited

U.S. PATENT DOCUMENTS

| | | |
|---|---|---|
| 6,799,074 B1 | 9/2004 | Thomas et al. |
| 6,920,347 B2 | 7/2005 | Simon et al. |
| 6,949,106 B2 | 9/2005 | Brock |
| 7,658,879 B2 | 2/2010 | Solar |
| 7,720,522 B2 | 5/2010 | Solar |
| 7,730,563 B1 | 6/2010 | Sklar et al. |
| 8,238,631 B2 | 8/2012 | Hartmann et al. |
| 2001/0018584 A1* | 8/2001 | Bays ............................. 604/516 |
| 2003/0181810 A1* | 9/2003 | Murphy et al. ............... 600/427 |
| 2005/0242055 A1 | 11/2005 | Oh |
| 2006/0282044 A1* | 12/2006 | Mohammed ......... A61B 5/1444 604/192 |
| 2007/0129629 A1 | 6/2007 | Beauregard et al. |
| 2008/0097193 A1* | 4/2008 | Karmarkar .................... 600/423 |
| 2008/0214922 A1 | 9/2008 | Hartmann et al. |
| 2008/0275466 A1* | 11/2008 | Skakoon ....................... 606/130 |
| 2009/0112084 A1* | 4/2009 | Piferi ................... A61N 1/0534 600/421 |
| 2009/0171184 A1 | 7/2009 | Jenkins et al. |
| 2010/0125240 A1 | 5/2010 | Spedden et al. |
| 2010/0160771 A1 | 6/2010 | Gielen et al. |
| 2010/0229414 A1 | 9/2010 | Nonni et al. |
| 2011/0083672 A1* | 4/2011 | Webster ............ A61M 16/0465 128/207.15 |
| 2011/0152860 A1 | 6/2011 | Morejohn et al. |
| 2012/0046542 A1 | 2/2012 | Casavoy et al. |

OTHER PUBLICATIONS

Extended European Search Report corresponding to European Application No. 14854336.6 dated Apr. 25, 2017.

* cited by examiner

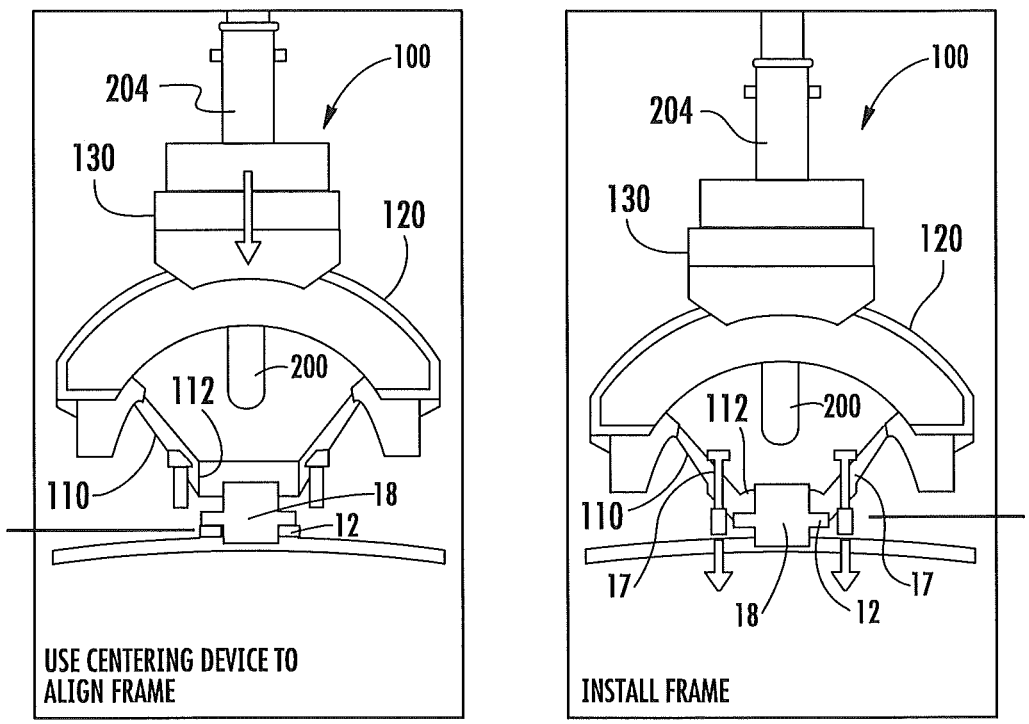
FIG. 3B
FIG. 3C
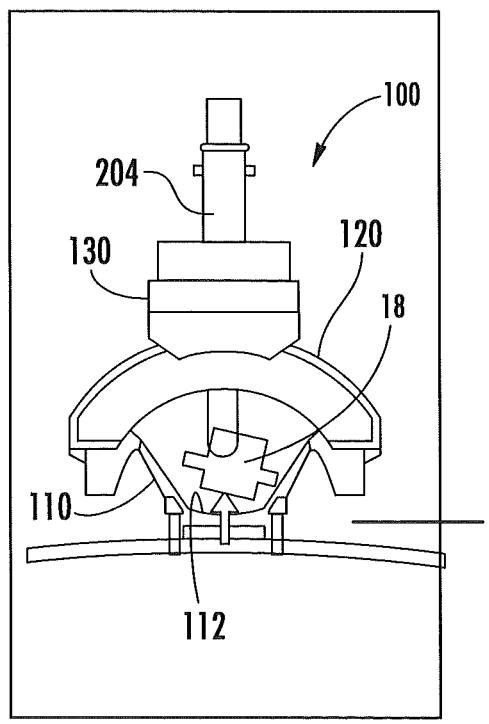
FIG. 3D

MRI-GUIDED MEDICAL INTERVENTIONAL SYSTEMS AND METHODS

RELATED APPLICATION

This application claims the benefit of and priority to U.S. Provisional Patent Application No. 61/673,583 filed Jul. 19, 2012, the disclosure of which is incorporated herein by reference as if set forth in its entirety.

FIELD OF THE INVENTION

The present invention relates generally to medical systems and methods and, more particularly, to in vivo medical systems and methods.

BACKGROUND

During MRI-Guided surgeries, it can be desired to drill through bone such as a skull to define a surgical path for passing medical interventional devices.

SUMMARY

Embodiments of the present invention provide methods, devices and systems for localized placement and/or delivery of diagnostic or therapeutic devices or substances.

According to embodiments of the present invention, an MRI-guided interventional system includes a frame with a removable, cooperating targeting cannula. The frame is configured to be secured to the body of a patient, and is configured to translate and rotate such that the targeting cannula can be positioned to a desired intrabody trajectory. The frame may include one or more MRI-visible fiducial markers that allow frame location/orientation to be determined within an MRI image.

Embodiments of the present invention may be particularly suitable for placing neuro-modulation leads, such as Deep Brain Stimulation ("DBS") leads, implantable parasympathetic or sympathetic nerve chain leads and/or CNS stimulation leads, as well as other devices within the brain.

Embodiments of the present invention may be suitable for a number of interventional procedures in many locations inside the body including, but not limited to, brain, cardiac, spinal, urethral, and the like.

Embodiments of the present invention may be suitable for a number of MRI-guided drug delivery procedures to intra-brain or other intra-body targeted locations.

Embodiments of the present invention may be suitable for a number of MRI-guided ablation procedures.

A plurality of user-activatable actuators are operably connected to the frame and are configured to translate and rotate the frame relative to the body of a patient so as to position the targeting cannula to a desired intrabody trajectory. In some embodiments, the actuators are dials or thumb-screw-type devices that allow manual manipulation thereof. In other embodiments, the actuators are manipulated remotely using remote controls and cables.

The removable targeting cannula includes an axially-extending guide bore therethrough that is configured to guide placement of an interventional device in vivo. Various instrumentation and equipment (e.g., stimulation leads, ablation probes or catheters, injection or fluid delivery devices, biopsy needles, extraction tools, etc.) can be inserted through the targeting cannula to execute diagnostic and/or surgical procedures.

According to some embodiments of the present invention, the frame includes a base, a yoke movably mounted to the base and that is rotatable about a roll axis, and a platform movably mounted to the yoke and that is rotatable about a pitch axis. The platform includes an X-Y support table that is configured to move in an X-direction and Y-direction relative to the platform. The base has a patient access aperture formed therein, and is configured to be secured to the body of a patient such that the aperture overlies an opening in the body. A roll actuator is operably connected to the yoke and is configured to rotate the yoke about the roll axis. A pitch actuator is operably connected to the platform and is configured to rotate the platform about the pitch axis. An X-direction actuator is operably connected to the platform and is configured to move the X-Y support table in the X-direction. A Y-direction actuator is operably connected to the platform and is configured to move the X-Y support table in the Y-direction.

The base may include a plurality of locations for attachment to a body of a patient via fasteners. In some embodiments, one or more attachment locations may include multiple adjacent apertures configured to receive a fastener therethrough. For embodiments where the frame is configured to be attached to the skull of a patient, the base can be configured to be secured to the skull of a patient such that the patient access aperture overlies a burr hole formed in the patient skull.

According to some embodiments of the present invention, the yoke includes a pair of spaced apart arcuate arms. The platform engages and moves along the yoke arcuate arms when rotated about the pitch axis. The base includes at least one arcuate arm. The yoke engages and moves along the base arcuate arm when rotated about the roll axis.

According to some embodiments of the present invention, at least one of the yoke arcuate arms includes a thread pattern formed in a surface thereof. The pitch actuator includes a rotatable worm with teeth configured to engage the thread pattern. Rotation of the worm causes the platform to rotate about the pitch axis. Similarly, at least one of the base arcuate arms includes a thread pattern formed in a surface thereof. The roll actuator includes a rotatable worm with teeth configured to engage the thread pattern, and wherein rotation of the worm causes the yoke to rotate about the roll axis.

In some embodiments, the actuators are color-coded such that each different actuator has a respective different color. This allows a user to quickly determine which actuator is the correct one for a particular desired movement of the frame.

An elongated tubular guide extends through the platform and yoke along a Z-direction and includes opposite proximal and distal end portions. The guide distal end portion is positioned proximate the patient access aperture. The guide includes a bore therethrough that extends from the proximal end portion to the distal end portion, and the guide is configured to removably receive different devices within the bore. The devices may have different sizes and configuration. Exemplary devices include a targeting cannula a drill guide and drill bit, a skull fixation device and driver, a catheter guide, etc.

In some embodiments of the present invention, the guide proximal end portion includes threads formed therein that are configured to threadingly engage a portion of a device inserted within the guide for quick release therefrom. In other embodiments of the present invention, the guide proximal end portion is configured to removably retain a portion of a device inserted within the guide for quick release therefrom, without the use of threads. For example, the guide proximal end portion may include a detent, or other type of structure (shape and/or component), formed therein, and a device includes a portion having a protrusion configured to engage the detent so as to removably secure the device to the guide via a snap fit. Alternatively, the guide proximal end portion may include a protrusion and the device may include a portion having a detent formed therein that is configured to engage the protrusion so as to removably secure the device to the guide via a snap fit. The term "quick release", as used herein, means that a technician or other user can quickly remove a device from the guide with little effort and without requiring tools.

According to some embodiments of the present invention, an MRI medical assembly includes a trajectory frame and a plurality of devices that are releasably and serially inserted within the frame so as to be positioned adjacent to a body of a patient. Exemplary devices include a targeting cannula, a drill guide and drill bit, a skull fixation device and driver, and a catheter guide.

The frame includes a base configured to be secured to the body of a patient and having a patient access aperture formed therein, a yoke movably mounted to the base and rotatable about a roll axis, and a platform movably mounted to the yoke and rotatable about a pitch axis. The platform may include an X-Y support table movably mounted thereto that is configured to move in an X-direction and Y-direction relative to the platform. An elongated guide is secured to the X-Y support table and includes opposite proximal and distal end portions, and a bore therethrough that extends from the proximal end portion to the distal end portion. The guide distal end portion is positioned proximate the patient access aperture. A device is inserted within the bore, and includes opposite proximal and distal end portions. The device distal end portion is positioned proximate the patient access aperture, and the device proximal end portion is removably secured to the guide proximal end portion.

In some embodiments, the guide proximal end portion includes threads formed therein, and the device comprises a portion configured to threadingly engage the guide proximal end portion. In other embodiments, the device may include a portion configured to be removably secured to the guide proximal end portion via a snap fit. In yet further embodiments, the guide proximal end portion includes at least one slot and the device is removably secured within the guide bore via at least one member extending outwardly from the device that cooperates with the at least one slot.

In some embodiments, the guide is removably secured to the X-Y support table such that the guide can be removed and replaced with another guide of a different size/configuration.

According to some embodiments of the present invention, an MRI interventional method includes affixing a frame with a cooperating guide to the skull of a patient, removably securing a targeting cannula within the guide, inserting a punch into the targeting cannula, creating an incision in the skull of the patient via the punch, and removing the punch and targeting cannula from the guide. The method further includes removably securing a drill guide within the guide, inserting a drill bit within the lumen of the drill guide, and drilling a hole within the skull of the patient at the incision via the drill bit. The method further includes removing the drill guide and drill bit from the targeting cannula, removably securing a skull fixation device to a distal end of the targeting cannula guide, removably inserting a skull fixation device driver within the targeting cannula guide, wherein the skull fixation device driver is configured to cooperate with the skull fixation device, and rotating the skull fixation device driver to cause the skull fixation device to be inserted within the hole in the skull of the patient. The skull fixation device driver is removed from the guide, a catheter guide is removably secured within the guide, and a catheter is advanced through the catheter guide.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail below.

BRIEF DESCRIPTION OF THE DRAWINGS

FIGS. 3B-3E are side view, schematic, sequential illustrations of a trajectory frame being secured to the skull of a patient.

DETAILED DESCRIPTION

Figure 1A:
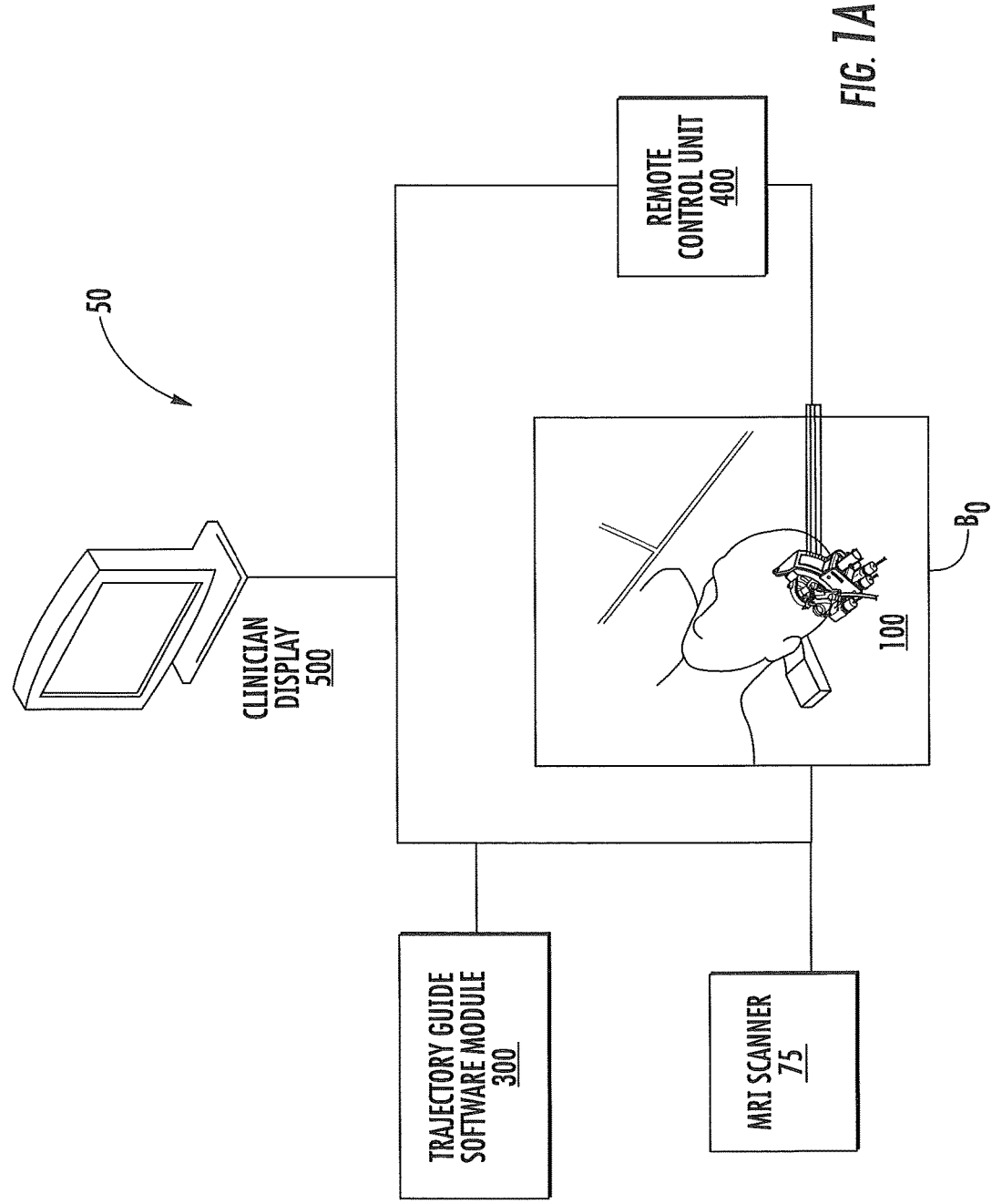
FIG. 1A is a block diagram of an MRI-guided interventional system, according to some embodiments of the present invention.

The present invention now is described more fully hereinafter with reference to the accompanying drawings, in which some embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

The term "about", as used herein with respect to a value or number, means that the value or number can vary by +/− twenty percent (20%).

The term "MRI visible" means that a device is visible, directly or indirectly, in an MRI image. The visibility may be indicated by the increased SNR of the MRI signal proximate to the device (the device can act as an MRI receive antenna to collect signal from local tissue) and/or that the device actually generates MRI signal itself, such as via suitable hydro-based coatings and/or fluid (typically aqueous solutions) filled channels or lumens.

The term "MRI compatible" means that a device is safe for use in an MRI environment and/or can operate as intended in an MRI environment without generating MR signal artifacts, and, as such, if residing within the high-field strength region of the magnetic field, is typically made of a non-ferromagnetic MRI compatible material(s) suitable to reside and/or operate in a high magnetic field environment.

The term "high-magnetic field" refers to field strengths above about 0.5 T (Tesla), typically above 1.0 T, and more typically between about 1.5 T and 10 T.

The term "targeting cannula" refers to an elongate device, typically having a substantially tubular body that can be oriented to provide positional data relevant to a target treatment site and/or define a desired access path orientation or trajectory. At least portions of a targeting cannula contemplated by embodiments of the invention can be configured to be visible in an MRI image, thereby allowing a clinician to visualize the location and orientation of the targeting cannula in vivo relative to fiducial and/or internal tissue landscape features. Thus, the term "cannula" refers to an elongate device that can be associated with a trajectory frame that attaches to a patient, but does not necessarily enter the body of a patient.

The term "imaging coils" refers to a device that is configured to operate as an MRI receive antenna. The term "coil" with respect to imaging coils is not limited to a coil shape but is used generically to refer to MRI antenna configurations, loopless, looped, etc., as are known to those of skill in the art. The term "fluid-filled" means that the component includes an amount of the fluid but does not require that the fluid totally, or even substantially, fill the component or a space associated with the component. The fluid may be an aqueous solution, MR contrast agent, or any material that generates MRI signal.

The term "two degrees of freedom" means that a trajectory frame described herein allows for at least translational (swivel or tilt) and rotational movement over a fixed site, which may be referred to as a Remote Center of Motion (RCM).

Embodiments of the present invention can be configured to guide and/or place diagnostic or interventional devices and/or therapies to any desired internal region of the body or object using MRI and/or in an MRI scanner or MRI interventional suite. The object can be any object, and may be particularly suitable for animal and/or human subjects. Some embodiments can be sized and configured to place implantable DBS leads for brain stimulation, typically deep brain stimulation. Some embodiments can be configured to deliver tools or therapies that stimulate a desired region of the sympathetic nerve chain. Other uses inside or outside the brain include stem cell placement, gene therapy or drug delivery for treating physiological conditions. Some embodiments can be used to treat tumors. Some embodiments can be used for RF ablation, laser ablation, cryogenic ablation, etc. In some embodiments, the trajectory frame and/or interventional tools can be configured to facilitate high resolution imaging via integral intrabody imaging coils (receive antennas), high intensity focused ultrasound (HIFU), and/or the interventional tools can be configured to stimulate local tissue, which can facilitate confirmation of proper location by generating a physiologic feedback (observed physical reaction or via fMRI).

Some embodiments can be used to deliver bions, stem cells or other target cells to site-specific regions in the body, such as neurological target sites and the like. In some embodiments, the systems deliver stem cells and/or other cardio-rebuilding cells or products into cardiac tissue, such as a heart wall via a minimally invasive MRI guided procedure, while the heart is beating (i.e., not requiring a non-beating heart with the patient on a heart-lung machine). Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Generally stated, some embodiments of the invention are directed to MRI interventional procedures and provide interventional tools and/or therapies that may be used to locally place interventional tools or therapies in vivo to site-specific regions using an MRI system. The interventional tools can be used to define an MRI-guided trajectory or access path to an in vivo treatment site. Some embodiments of the invention provide interventional tools that can provide positional data regarding location and orientation of a tool in 3-D space with a visual confirmation on an MRI. Embodiments of the invention may provide an integrated system that may allow physicians to place interventional devices/leads and/or therapies accurately and in shorter duration procedures over conventional systems (typically under six hours for DBS implantation procedures, such as between about 1-5 hours).

In some embodiments, MRI can be used to visualize (and/or locate) a therapeutic region of interest inside the brain or other body locations and to visualize (and/or locate) an interventional tool or tools that will be used to deliver therapy and/or to place a chronically implanted device that will deliver therapy. Then, using the three-dimensional data produced by an MRI-guided interventional system regarding the location of the therapeutic region of interest and the location of the interventional tool, the system and/or physician can make positional adjustments to the interventional tool so as to align the trajectory of the interventional tool with the region of interest, so that when inserted into the body, the interventional tool will intersect with the therapeutic region of interest. With the interventional tool now aligned with the therapeutic region of interest, an interventional probe can be advanced, such as through an open lumen inside of the interventional tool, so that the interventional probe follows the trajectory of the interventional tool and proceeds to the therapeutic region of interest. It should be noted that the interventional tool and the interventional probe may be part of the same component or structure. A sheath may optionally form the interventional tool or be used with an interventional probe or tool.

In particular embodiments, using MRI in combination with local or internal imaging coils and/or MRI contrast material that may be contained at least partially in and/or on the interventional probe or sheath, the location of the interventional probe within the therapeutic region of interest can be visualized on a display or image and allow the physician to either confirm that the probe is properly placed for delivery of the therapy (and/or placement of the implantable device that will deliver the therapy) or determine that the probe is in the incorrect or a non-optimal location. Assuming that the interventional probe is in the proper desired location, the therapy can be delivered and/or the interventional probe can be removed and replaced with a permanently implanted therapeutic device at the same location.

In some embodiments, in the event that the physician determines from the MRI image produced by the MRI and the imaging coils, which may optionally be contained in or on the interventional probe, that the interventional probe is not in the proper location, a new therapeutic target region can be determined from the MRI images, and the system can be updated to note the coordinates of the new target region. The interventional probe is typically removed (e.g., from the brain) and the interventional tool can be repositioned so that it is aligned with the new target area. The interventional probe can be reinserted on a trajectory to intersect with the new target region. Although described and illustrated herein with respect to the brain and the insertion of deep brain stimulation leads, it is understood that embodiments of the present invention may be utilized at other portions of the body and for various other types of procedures.

Embodiments of the present invention will now be described in detail below with reference to the figures. FIG. 1A is a block diagram of an MRI-guided interventional system 50, according to some embodiments of the present invention. The illustrated system 50 includes an MRI scanner 75, a trajectory frame 100 attached to the body of a patient positioned within a magnetic field $B_0$ of the MRI scanner 75, a remote control unit 400, a trajectory guide software module 300, and a clinician display 500. The trajectory frame 100 is configured to support various devices including a targeting cannula through which various interventional devices may be inserted into the body of a patient. The frame 100 is adjustable such that the targeting cannula is rotatable about a pitch axis, about a roll axis, and such that the targeting cannula can translate in X-Y directions relative to a Z-direction defined by a guide configured to support devices such as a targeting cannula. The frame 100 may be attached to the body of a patient directly or indirectly and may be configured to be attached to various parts of the body.

Figure 1B:
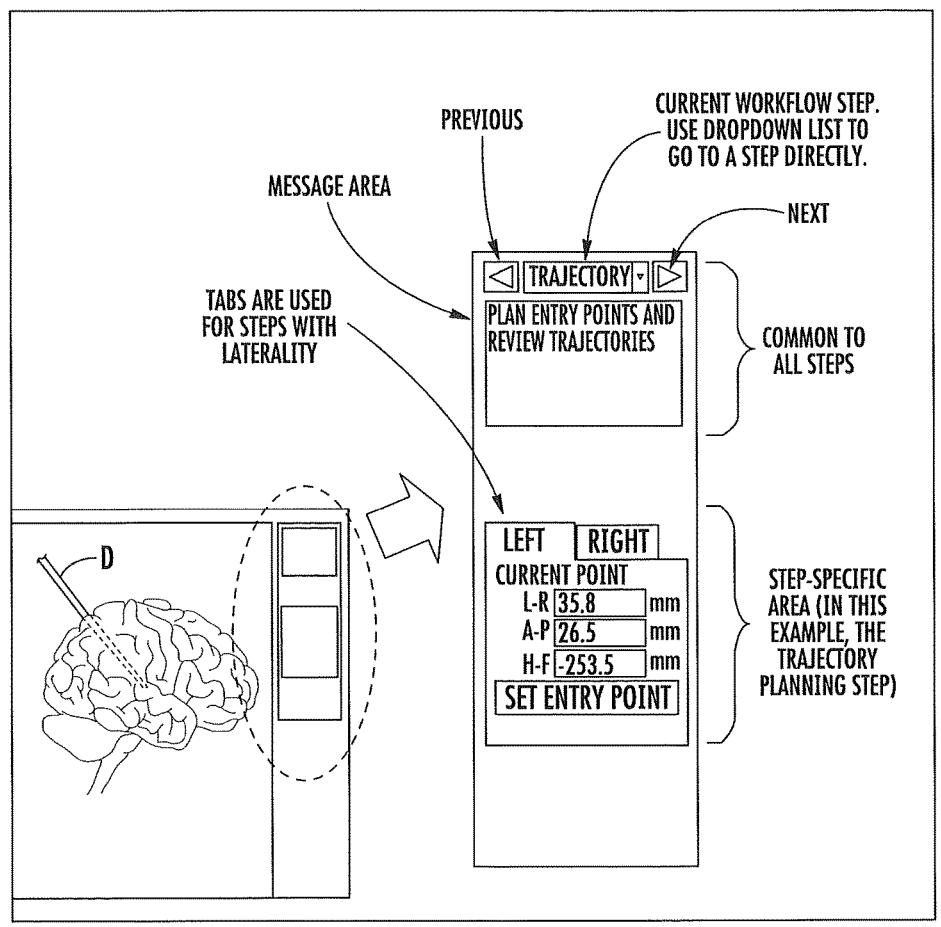
FIG. 1B illustrates a user interface that displays, and that allows a user to adjust, the trajectory of a targeting cannula, according to some embodiments of the present invention.
Figure 11:
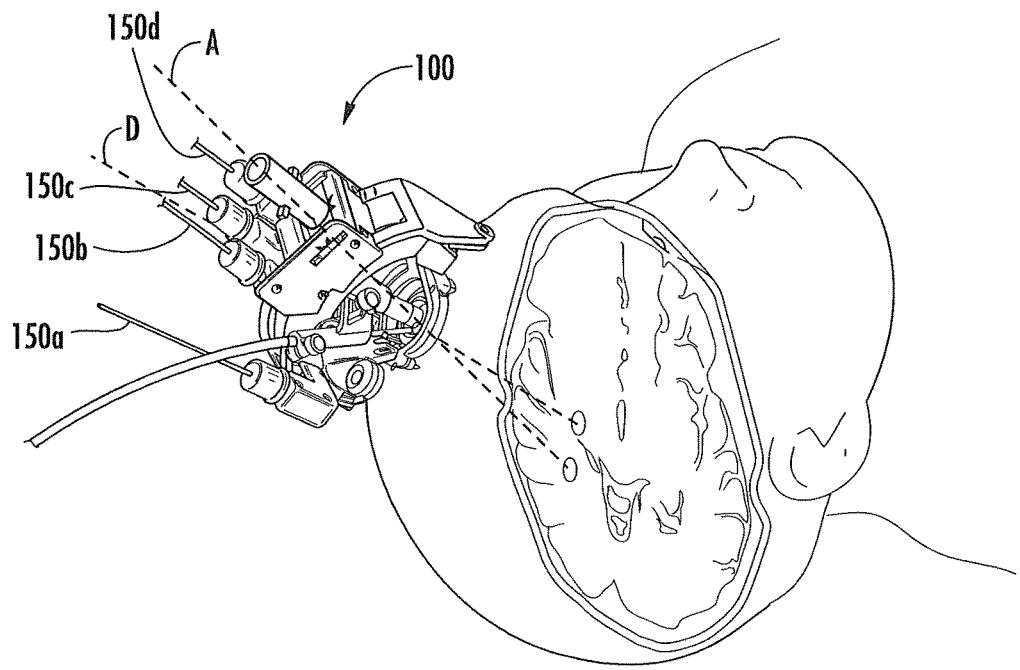
FIG. 11 illustrates the trajectory frame of FIG. 3A secured to the skull of a patient and illustrates a desired trajectory for an interventional device, and also illustrates the actual trajectory of the interventional device as oriented by the frame.
Figure 12:
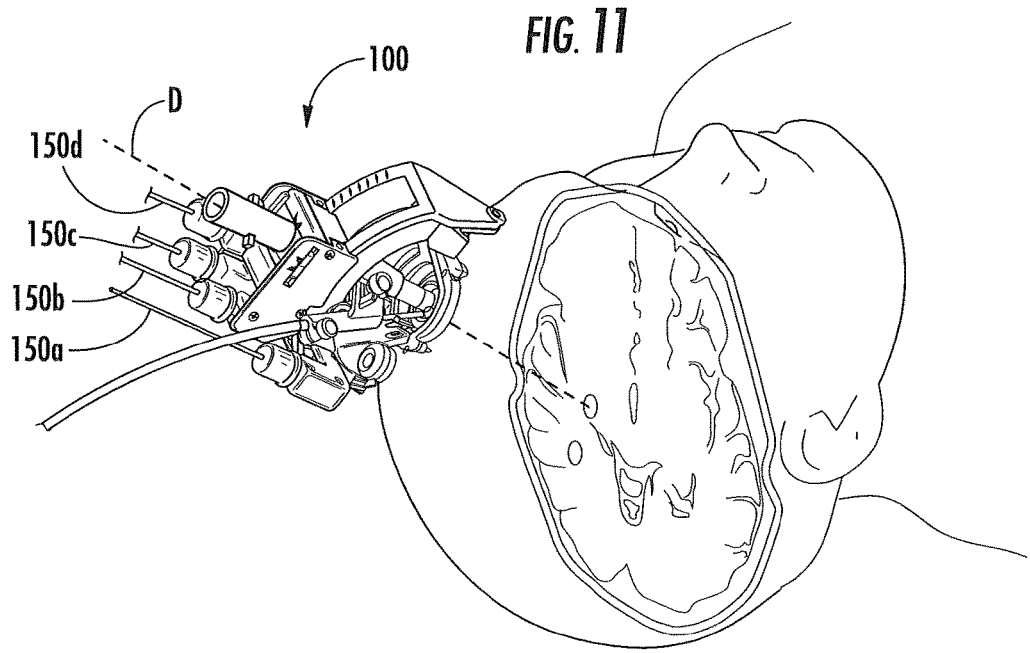
FIG. 12 illustrates the frame of FIG. 11 after reorientation via manipulation of one or more trajectory frame actuators such that the actual trajectory is adjusted to be in alignment with the desired trajectory.

In some embodiments, a remote control unit 400 is provided to allow a user to remotely adjust the position of the targeting cannula or other devices supported by the trajectory frame 100. The system 50 can include a trajectory guide software module 300 that allows a user to define and visualize, via display 500, a desired trajectory (D, FIGS. 1B, 11-12) into the body of a patient of an interventional device extending through the targeting cannula. The trajectory guide software module 300 also allows the user to visualize and display, via display 500, an actual trajectory (A, FIG. 11) into the body of an interventional device extending through the targeting cannula. The trajectory guide software module 300 displays to the user positional adjustments (FIG. 1B) (e.g., pitch axis rotation, roll axis rotation, X-Y translation) needed to align the actual trajectory of the targeting cannula with the desired trajectory path. In addition, the user can view, via display 500, the actual trajectory changing as he/she adjusts the position of the targeting cannula. The trajectory guide software module 300 can be configured to indicate and display when an actual trajectory is aligned with a desired trajectory.

Figure 2A:
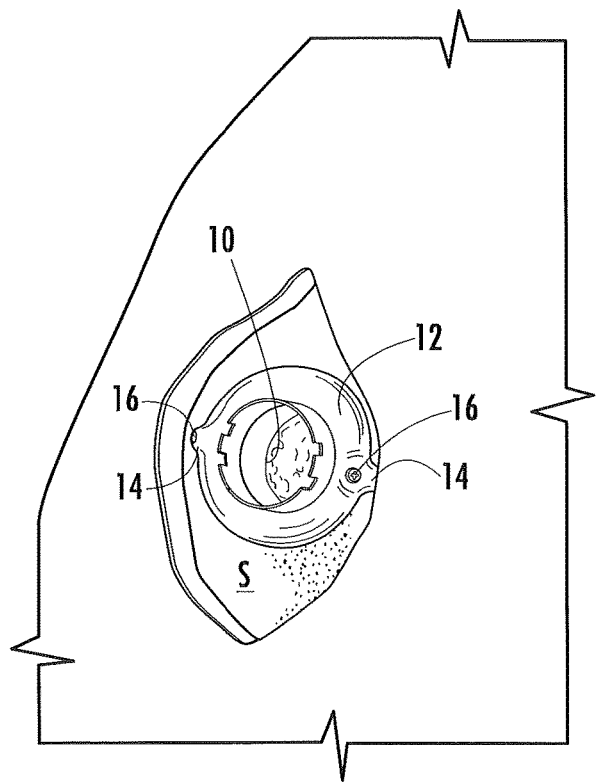
FIG. 2A is a top perspective view of a burr hole formed in the skull of a patient, and a burr hole ring overlying the burr hole and secured to the skull.

FIG. 2A illustrates a burr hole 10 formed in the skull S of a patient. A burr hole ring 12 overlies the burr hole 10 and is secured to the skull S. The illustrated burr hole ring 12 has at least one pair of ears 14, each ear configured to receive a respective fastener (e.g., screw) therethrough for securing the burr hole ring 12 to the skull. In the illustrated embodiment, the burr hole ring 12 is secured to the skull S via screws 16.

Figure 2B:
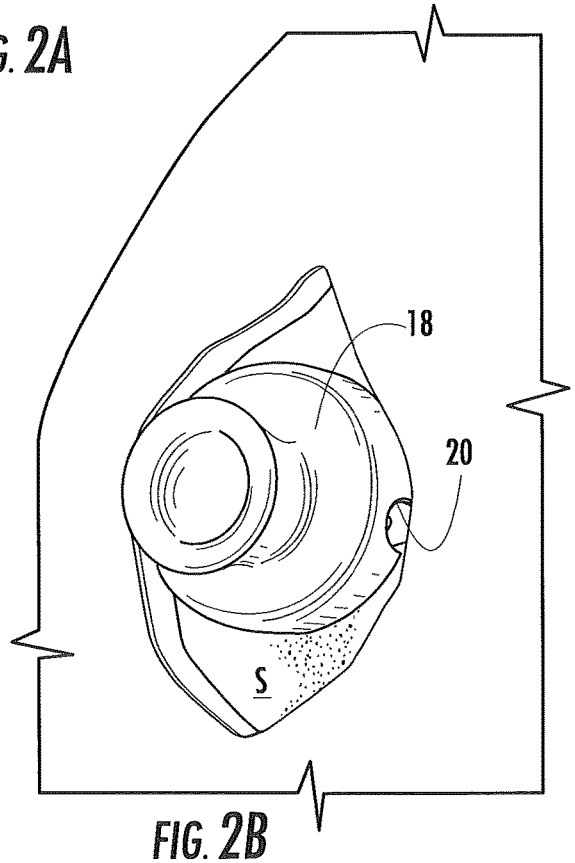
FIG. 2B is a top perspective view of a removable centering device positioned on the burr hole ring of FIG. 1.

FIG. 2B illustrates a removable centering device 18 positioned on the burr hole ring 12. The centering device 18 includes slots, channels, or other recessed or cut out portions 20 that fit over the ears 14 of the burr hole ring 12. The function of the centering device 18 is to facilitate centering a trajectory frame 100, described below, over the burr hole 10. After the trajectory frame 100 is attached to the skull of a patient, the centering device 18 is removed.

Figure 3A:
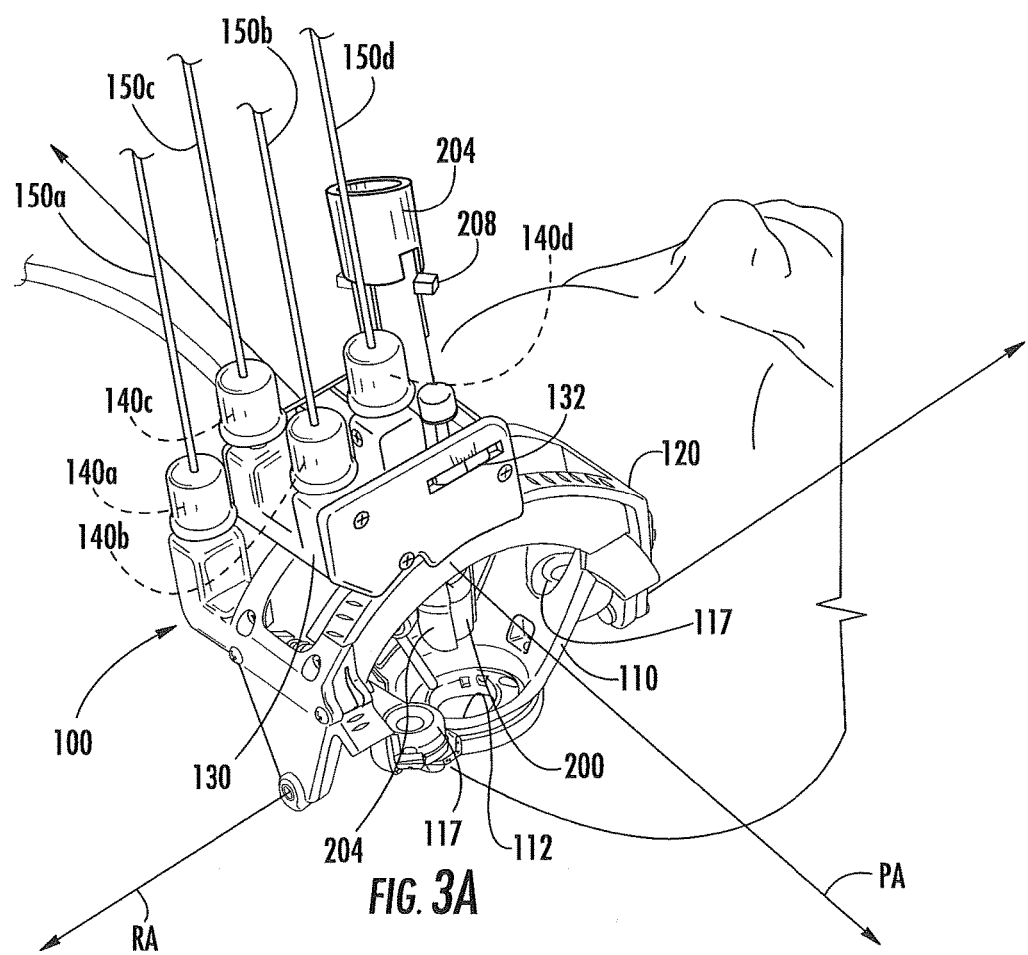
FIG. 3A is a top, side perspective view of a trajectory frame utilized in a MRI-guided interventional system, according to some embodiments of the present invention.
Figure 8A:
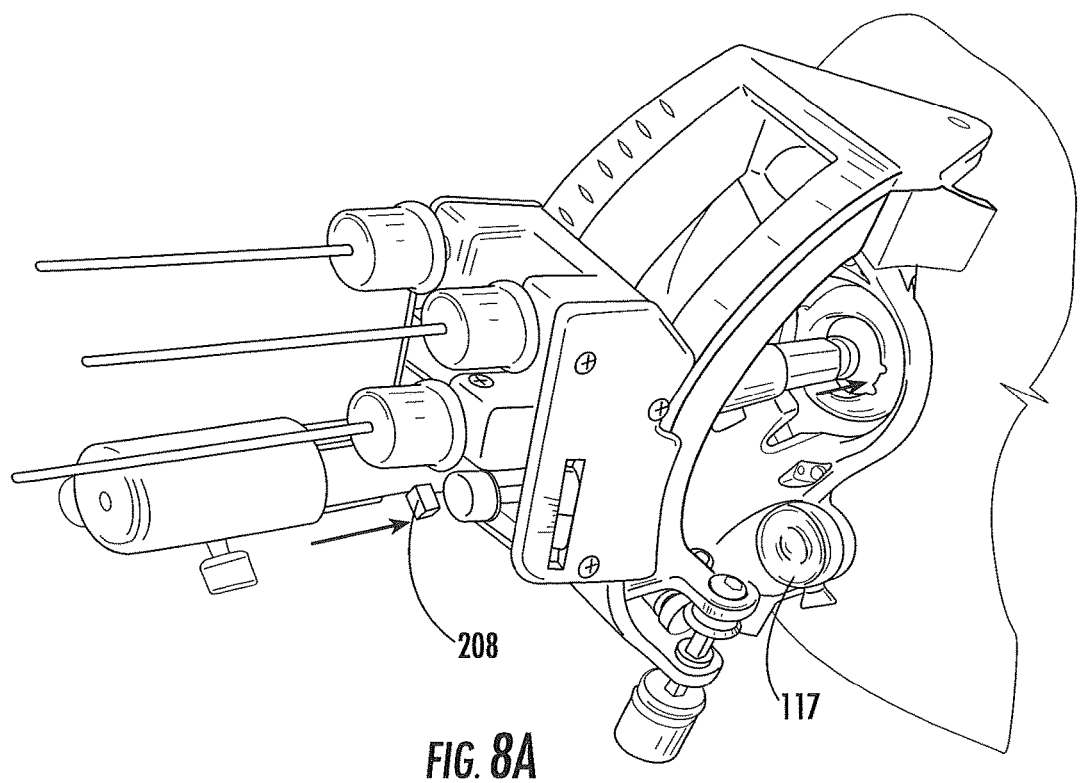
FIG. 8A is a perspective view of the trajectory frame of FIG. 3A secured to the body (e.g., skull) of a patient, and with the targeting cannula in an extended position.
Figure 8B:
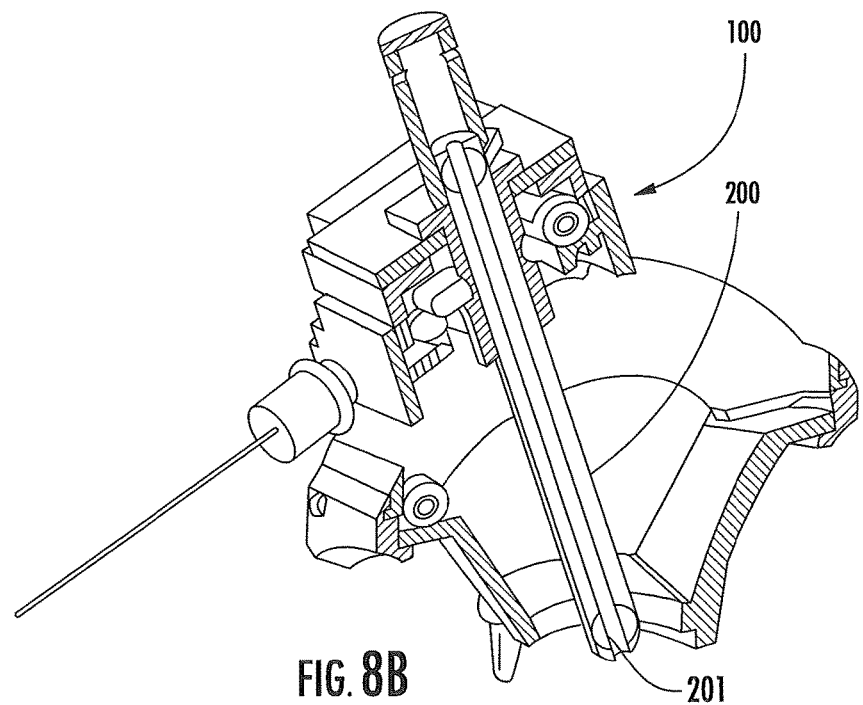
FIG. 8B is a cut-away perspective view of the trajectory frame of FIG. 3A, illustrating a guide with a targeting cannula therein according to some embodiments of the present invention.

Referring to FIG. 3A, a trajectory frame 100 with a targeting cannula 200 associated therewith is illustrated. The trajectory frame 100 includes a guide 204 (shown in partial view for ease of illustration) that removably receives the targeting cannula 200 therein. The guide 204 is secured to the X-Y support table 132 of the trajectory frame. The guide 204 defines a Z-direction along its longitudinal axis relative to the X-Y plane of the X-Y support table 132. The trajectory frame 100 allows for the adjustability (typically at least two degrees of freedom, including rotational and translational) and/or calibration/fixation of the trajectory of the targeting cannula 200 and/or probe or tool inserted through the targeting cannula 200. The targeting cannula 200 includes an axially-extending guide bore 201 (FIG. 8B) therethrough that is configured to guide the desired therapeutic or diagnostic tool, e.g., intra-brain placement of a stimulation lead (or other type of device) in vivo, as will be described below. Intra-brain placement of devices may include chronically placed devices and acutely placed devices. The trajectory frame 100 may include fiducial markers 117 that can be detected in an MRI to facilitate registration of position in an image.

The illustrated trajectory frame 100 is configured to be mounted to a patient's skull around a burr hole ring (12, FIG. 1) and over a burr hole (10, FIG. 1), to provide a stable platform for advancing surgical devices, leads, etc. in the brain. The trajectory frame 100 includes a base 110, a yoke 120, a platform 130, and a plurality of actuators 140a-140d. The base 110 has a patient access aperture 112 formed therein, as illustrated. The base 110 is configured to be secured (directly or indirectly) to the skull of a patient such that the patient access aperture 112 overlies the burr hole 10 in the patient skull. The patient access aperture 112 is centered over the burr hole 10 via the removable centering device 18. The yoke 120 is movably mounted to the base 110 and is rotatable about a roll axis RA. A roll actuator 140a is operably connected to the yoke 120 and is configured to rotate the yoke 120 about the roll axis RA, as will be described in detail below. In some embodiments, the yoke 120 has a range of motion about the roll axis RA of about seventy degrees (70°). However, other ranges, greater and lesser than 70°, are possible, e.g., any suitable angle typically between about 10°-90°, 30°-90°, etc. The illustrated platform 130 is movably mounted to the yoke 120 and is rotatable about a pitch axis PA. A pitch actuator 140b is operably connected to the platform 130 and is configured to rotate the platform 130 about the pitch axis PA. In some embodiments, the platform 130 has a range of motion about the pitch axis PA of about seventy degrees (70°). However, other ranges, greater and lesser than 70°, are possible, e.g., any suitable angle typically between about 10°-90°, 30°-90°, etc.

The illustrated platform 130 includes an X-Y support table 132 that is movably mounted to the platform 130. The X-Y support table 132 is configured to move in an X-direction and Y-direction relative to the platform 130 and relative to a Z-direction defined by the longitudinal axis of the guide 204. An X-direction actuator 140c is operably connected to the platform 130 and is configured to move the X-Y support table 132 in the X-direction. A Y-direction actuator 140d is operably connected to the platform 130 and is configured to move the X-Y support table 132 in the Y-direction. A pitch actuator 140b is operably connected to the platform 130 and is configured to rotate the platform 130 about the pitch axis PA.

The actuators 140a-140d are configured to translate and/or rotate portions of the trajectory frame 100. The targeting cannula 200 is configured to translate in response to translational movement of the X-Y support table 132 and to rotate in response to rotational movement of the yoke 120 and platform 130 to define different axial intrabody trajectories extending through the patient access aperture 112 in the frame base 110.

The actuators 140a-140d may be manually-operated devices, such as thumbscrews, in some embodiments. The thumbscrews can be mounted on the frame 100 or may reside remotely from the frame 100. A user may turn the actuators 140a-140d by hand to adjust the position of the frame 100 and, thereby, a trajectory of the targeting cannula 200. In other embodiments, the actuators 140a-140d are operably connected to a remote control unit 400 (FIG. 1A) via a respective plurality of non-ferromagnetic, flexible drive shafts or control cables 150a-150d (FIG. 3A). The remote control unit 400 (FIG. 1A) includes a plurality of position controls, and each cable 150a-150d is operably connected to a respective position control and to a respective actuator 140a-140d. Movement of a position control operates a respective actuator 140a-140d via a respective control cable 150a-150d. The cables 150a-150d may extend a suitable distance (e.g., between about 1-4 feet, etc.) to allow a clinician to adjust the settings on the trajectory frame 100 without moving a patient and from a position outside the bore of a magnet (where a closed bore magnet type is used) associated with an MRI scanner.

Figure 3E:
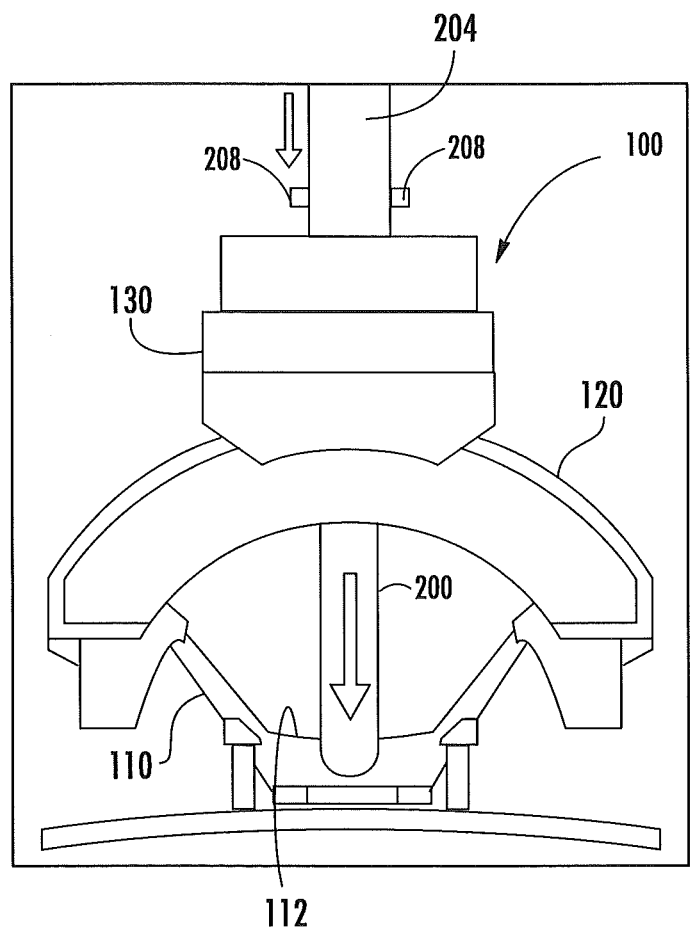

FIGS. 3B-3E are schematic side view sequential illustrations of the trajectory frame 100 being secured to the skull of a patient. FIG. 3B illustrates use of the centering device 18 to align the frame 100 relative to the burr hole 10. In FIG. 3C, the frame 100 is secured to the skull with fasteners and such that the patient access aperture 112 in the base 110 is centered around the centering device 18. In FIG. 3D, the yoke 120 is rotated out of the way such that the centering device 18 can be removed. In FIG. 3E, the targeting cannula 200 is moved to an extended position and locked in the extended position via prongs 208 that engage slots 1103 in the guide 204.

Figure 6:
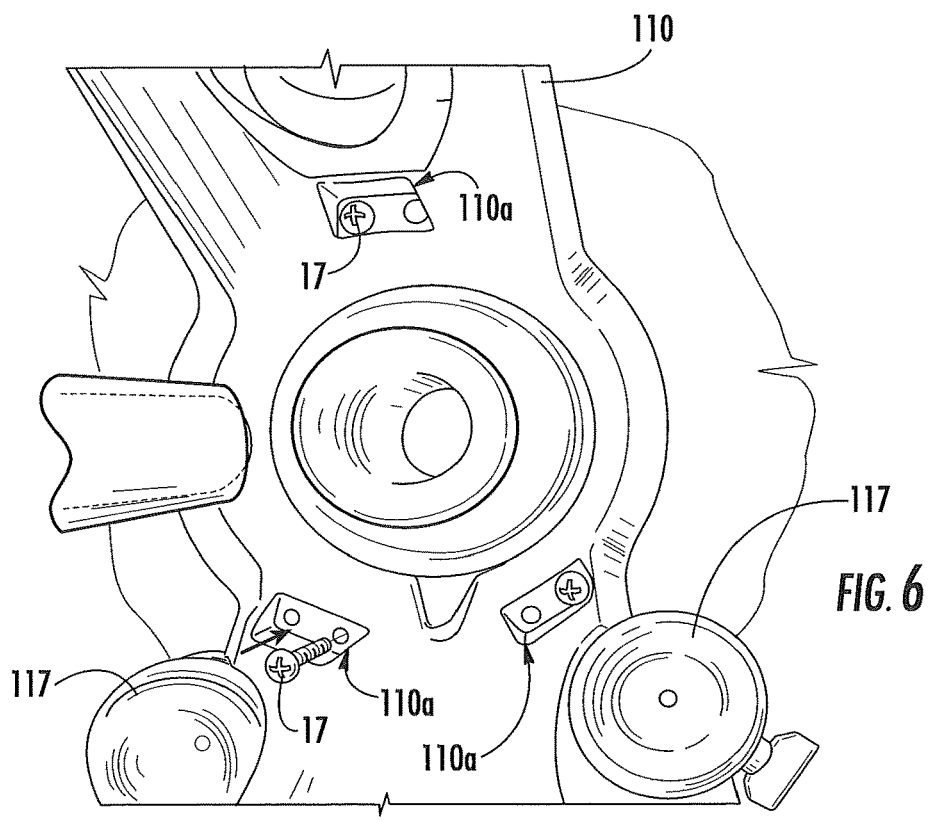
FIG. 6 illustrates the base of the trajectory frame of FIG. 3A secured to the skull of a patient.
Figure 7:
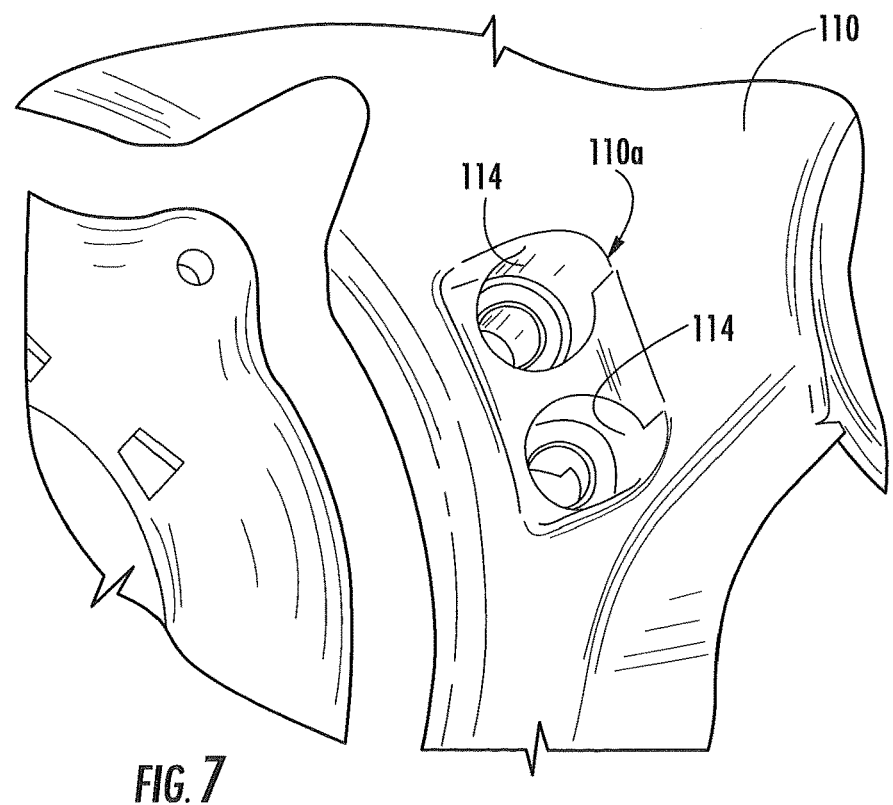
FIG. 7 is an enlarged partial perspective view of the base of the trajectory frame of FIG. 3A illustrating an attachment location with a pair of adjacent apertures for receiving fasteners therethrough, according to some embodiments of the present invention.

Referring to FIGS. 6-7, the base 110 includes a plurality of locations 110a for attaching the base 110 to a skull of a patient via fasteners 17. Each location 110a may include two or more adjacent apertures 114. Each aperture 114 is configured to receive a fastener 17 (e.g., a screw, rod, pin, etc.) therethrough that is configured to secure the base 110 to the skull of a patient.

The base 110 also includes MRI-visible fiducial markers 117 that allow the location/orientation of the trajectory frame 100 to be determined within an MRI image during an MRI-guided procedure. In the illustrated embodiment, the fiducial markers 117 have a torus or "doughnut" shape and are spaced apart. However, fiducial markers having various shapes and positioned at various locations on the trajectory frame 100 may be utilized.

Figure 4:
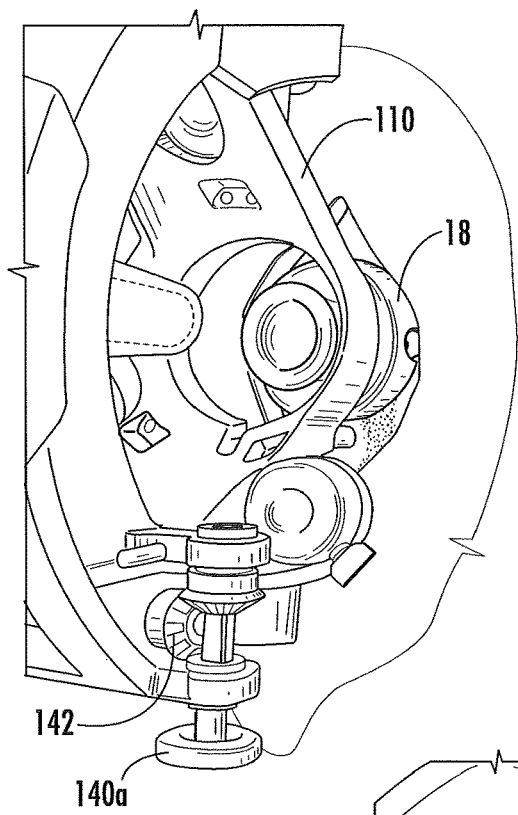
FIGS. 4-5 are partial top perspective views of the trajectory frame of FIG. 3A illustrating the base of the trajectory frame being positioned on the skull of a patient with the centering device of FIG. 2B extending through the patient access aperture.
Figure 5:
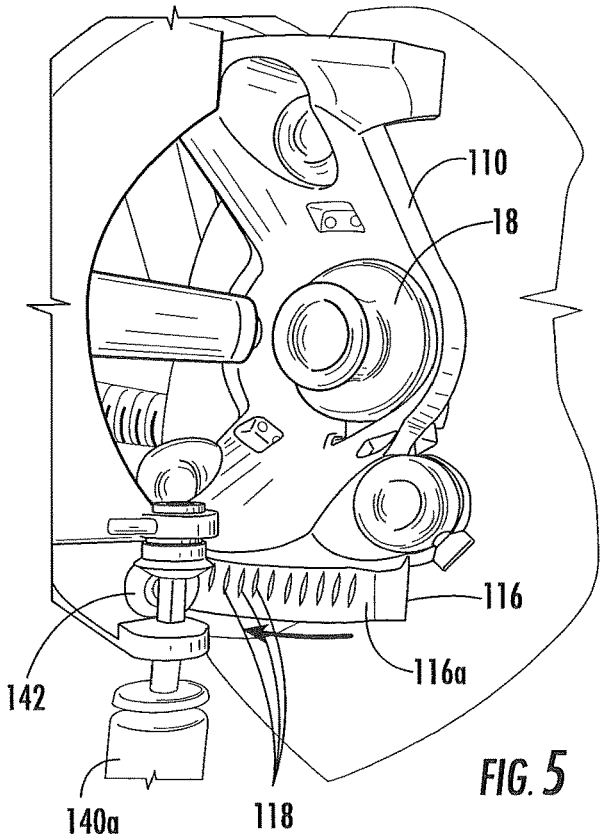
Figure 9:
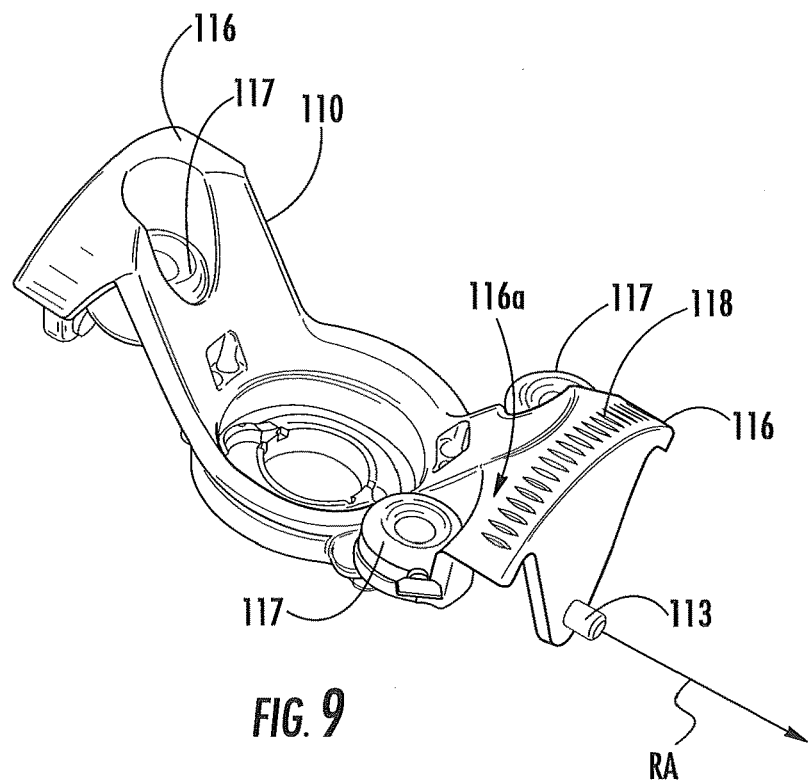
FIG. 9 is a perspective view of the base of the trajectory frame of FIG. 3A illustrating fiducial markers associated therewith and illustrating an arcuate arm with a thread pattern formed in a surface thereof that is configured to be engaged by a roll axis actuator, according to some embodiments of the present invention.

The base 110 also includes a pair of spaced apart arcuate arms 116, as illustrated in FIG. 9. The yoke 120 (FIG. 3A) is pivotally attached to pivot points 113 (FIG. 9) for rotation about the roll axis RA. The yoke 120 engages and moves along the base arcuate arms 116 when rotated about the roll axis RA. In the illustrated embodiment, one of the base arcuate arms 116 includes a thread pattern 118 formed in (e.g., embossed within, machined within, etc.) a surface 116a thereof. However, in other embodiments, both arms 116 may include respective thread patterns. The roll actuator 140a includes a rotatable worm 142 with teeth that are configured to engage the thread pattern 118, as illustrated in FIG. 5. As the worm 142 is rotated, the teeth travel along the thread pattern 118 in the arcuate arm surface 116a. Because the base 110 is fixed to a patient's skull, rotation of the roll actuator worm 142 causes the yoke 120 to rotate about the roll axis RA relative to the fixed base 110. Rotation about roll axis RA is illustrated in FIGS. 4-5. For example, in FIG. 5, the yoke 120 is rotated about the roll axis RA sufficiently to allow access to and removal of the centering device 18.

Figure 10:
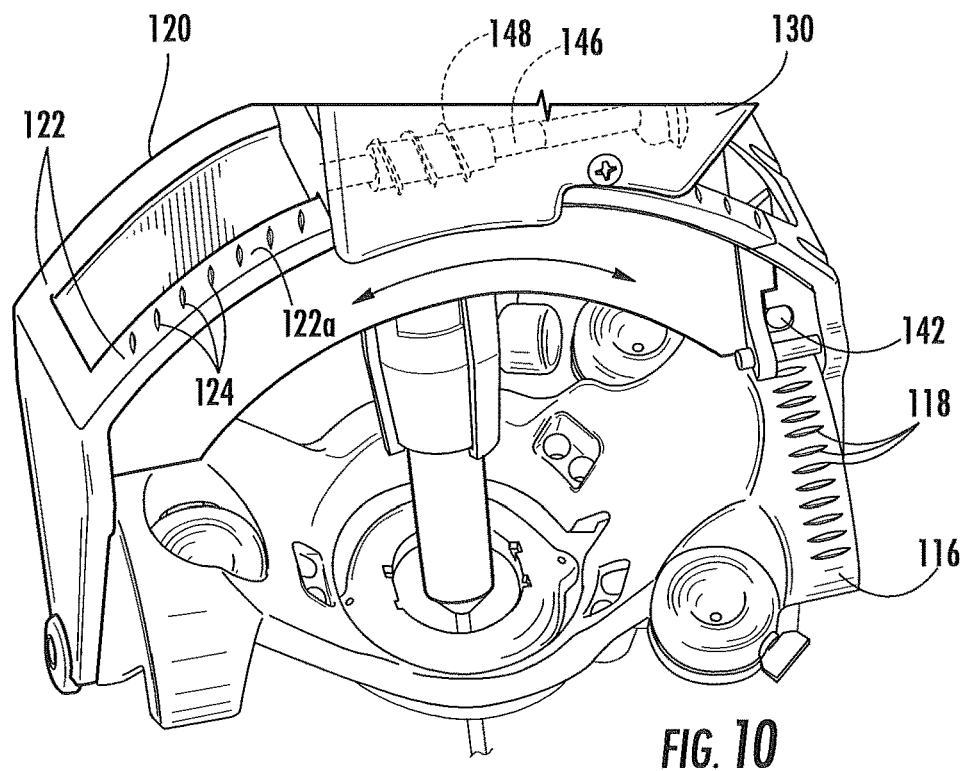
FIG. 10 is a partial perspective view of the trajectory frame of FIG. 3A illustrating a yoke arcuate arm with a thread pattern formed in a surface thereof that is configured to be engaged by a pitch axis actuator, according to some embodiments of the present invention.

Referring to FIG. 10, the yoke 120 includes a pair of spaced apart upwardly extending, arcuate arms 122. The platform 130 engages and moves along the yoke arcuate arms 122 when rotated about the pitch axis PA. In the illustrated embodiment, one of the yoke arcuate arms 122 includes a thread pattern 124 formed in (e.g., embossed within, machined within, etc.) a surface 122a thereof. However, in other embodiments, both arms 122 may include respective thread patterns. The pitch actuator 140b includes a rotatable worm 146 with teeth 148 that are configured to engage the thread pattern 124. As the worm 146 is rotated, the teeth 148 travel along the thread pattern 124 in the arcuate arm surface 122a. Because the base 110 is fixed to a patient's skull, rotation of the pitch actuator worm 146 causes the platform 130 to rotate about the pitch axis PA relative to the fixed base 110.

As illustrated in FIG. 3A, the roll actuator 140a, pitch actuator 140b, X-direction actuator 140c, and Y-direction actuator 140d each extend outwardly from the frame 100 along substantially the same direction (e.g., upwardly from the platform 130). This configuration facilitates easy connection of the control cables 150a-150d to the actuators 140a-140d (where used) and also facilitates bundling of the cables 150a-150d to reduce clutter or provide ease of handling and set-up. Embodiments of the present invention are not limited to the orientation/arrangement of the actuators 140a-140d and cables 150a-150d, however. The actuators 140a-140d may extend in various directions and these directions may be different from each other. In addition, the actuators 140a-140d may extend along the same direction from the frame, but in a different direction than that illustrated in FIG. 3A.

Operations associated with a typical surgical procedure using the trajectory frame 100, according to some embodiments of the present invention, will now be described. These operations relate to deep brain stimulation procedures. Embodiments of the present invention are not limited to use with deep brain stimulation procedures, however.

Initially, a patient is placed within an MR scanner and MR images are obtained of the patient's head that visualize the patient's skull, brain, fiducial markers and ROI (region of interest or target therapeutic site). The MR images can include volumetric high-resolution images of the brain. To identify the target ROI, certain known anatomical landmarks can be used, i.e., reference to the AC, PC and MCP points (brain atlases give the location of different anatomies in the brain with respect to these points) and other anatomical landmarks. The location of a burr hole 10 (FIG. 2A) may optionally be determined manually by placing fiducial markers on the surface of the head or programmatically by projecting the location in an image.

Images in the planned plane of trajectory are obtained to confirm that the trajectory is viable, i.e., that no complications with anatomically sensitive areas should occur. The patient's skull is optically or manually marked in one or more desired locations to drill the burr hole. The burr hole 10 is drilled and a burr hole ring 12 is affixed to the skull overlying the burr hole.

The trajectory frame 100 is then fixed to the skull of the patient and the targeting cannula 200 is properly fitted thereto. A localization scan can be obtained to determine/register the location of the targeting cannula 200, in direct orientation of the trajectory frame 100. The settings to which the trajectory frame 100 should be adjusted are electronically determined so that the targeting cannula 200 is in the desired trajectory plane. Frame adjustment calculations are provided to a clinician who can manually or electronically adjust the orientation of the trajectory frame 100. The desired trajectory plane is confirmed by imaging in one or more planes orthogonal to the desired trajectory plane.

Once the targeting cannula 200 has the desired trajectory plane, a multipurpose probe (not shown) and delivery sheath (not shown) can be advanced through the targeting cannula 200. The advancement of the probe can be monitored by imaging to verify that the probe will reach the target accurately. If the probe and delivery sheath are at the desired target, the sheath is left in place and the probe is removed. The sheath can now act as the delivery cannula for an implantable lead (not shown).

If the probe and delivery sheath are not at the desired/optimal location, a decision is made as to where the probe and delivery sheath need to be. The trajectory frame 100 is adjusted accordingly via the actuators 140a-140d and the probe and delivery sheath are re-advanced into the brain. Once the probe and delivery sheath are at the desired location, the probe is removed and the delivery sheath is left in place. A lead is then advanced to the target location using the sheath as a guide. The location of the lead is confirmed by reviewing an image, acoustic recording and/or stimulation. The sheath is then removed, leaving the lead in place.

It is contemplated that embodiments of the invention can provide an integrated system 50 that may allow the physician to place the interventional device/leads accurately and in short duration of time. In some embodiments, once the burr hole is drilled, and the trajectory frame is fixed to the skull; the trajectory frame is oriented such that the interventional device advanced using the trajectory frame follows the desired trajectory and reaches the target as planned in preoperative setup imaging plans. As described herein, the system 50 can employ hardware and software components to facilitate an automated or semiautomated operation to carry out this objective.

Referring now to FIGS. 13-19, a trajectory frame 1100, according to other embodiments of the present invention, is illustrated. The trajectory frame 1100 is similar to the trajectory frame 100 described above with respect to FIGS. 1A-12, but is configured to removably receive a targeting cannula and other devices of various sizes and configurations within a guide 1102, as described below. The illustrated trajectory frame 1100 is configured to be mounted to a patient's skull around a burr hole ring (12, FIG. 1) and over a burr hole (10, FIG. 1), to provide a stable platform for advancing surgical devices, leads, etc., in the brain, as described above. However, a trajectory frame 1100 according to embodiments of the present invention can be configured to be mounted to various portions of the body of a patient.

The illustrated trajectory frame 1100 includes a base 110, a yoke, 120, a platform 130, and a plurality of actuators 140a-140d, as described above. The base 110 has a patient access aperture 112 formed therein, as illustrated. The base 110 is configured to be secured (directly or indirectly) to the skull of a patient such that the patient access aperture 112 overlies the burr hole 10 in the patient skull. The base 110 includes a plurality of narrow, tapered members 19 that can be driven into the skull of a patient to prevent the base 110 from moving. Fasteners 17, such as screws, are then used to secure the base to the skull of the patient, as described above.

The patient access aperture 112 is configured to be centered over a burr hole 10 via a removable centering device 18, as described above. The yoke 120 is movably mounted to the base 110 and is rotatable about a roll axis RA, as described above. The platform 130 is movably mounted to the yoke 120 and is rotatable about a pitch axis PA, as described above.

The illustrated platform 130 includes an X-Y support table 132 that is movably mounted to the platform 130. The X-Y support table 132 is configured to move in an X-direction and Y-direction relative to the platform 130 and to a Z-direction defined by the longitudinal axis of the guide 1102. An X-direction actuator 140c is operably connected to the platform 130 and is configured to move the X-Y support table 132 in the X-direction. A Y-direction actuator 140d is operably connected to the platform 130 and is configured to move the X-Y support table 132 in the Y-direction. A pitch actuator 140b is operably connected to the platform 130 and is configured to rotate the platform 130 about the pitch axis PA.

The actuators 140a-140d are configured to translate and/or rotate the frame. When inserted within the guide 1102, the targeting cannula 200, and other devices inserted within the guide 1102, are configured to translate in response to translational movement of the X-Y support table 132 and to rotate in response to rotational movement of the yoke 120 and platform 130 to define different axial intrabody trajectories extending through the patient access aperture 112 in the frame base 110.

The trajectory frame guide 1102 is configured to removably receive various probes and/or tools, as described below. For example, the guide 1102 may have a larger diameter than conventional targeting cannula guides which, thereby allows for various devices to be utilized with the frame 1100 that otherwise would not be able to do so.

In addition, guides 1102 having different size internal diameters may be provided for receiving various devices of different sizes. For example, a guide 1102 may have an internal diameter sized to receive a particular device therein. Another guide 1102 may have a larger or smaller internal diameter also sized to receive a particular device therein. To facilitate replacing one size guide 1102 with another, each guide 1102 may be removably secured to the X-Y support table 132. For example, each guide may be threadingly secured to the X-Y support table 132. However, other means for removably securing a guide 1102 to the X-Y support table can be utilized.

The trajectory frame 1100 allows for the adjustability (typically at least two degrees of freedom, including rotational and translational) and calibration/fixation of the trajectory of a targeting cannula 200 and/or probe or tool inserted through the guide 1102. The removable targeting cannula 200 has a proximal end portion 200a, an opposite distal end portion 200b, and an axially-extending guide bore 201 extending from the proximal end portion 200a to the distal end portion 200b that is configured to guide a therapeutic or diagnostic tool, e.g., intra-brain placement of a stimulation lead (or other type of device) in vivo. Intra-brain placement of devices may include chronically placed devices and acutely placed devices. The trajectory frame 1100 also include fiducial markers 117 that can be detected in an MRI to facilitate registration of position in an image. Lugs 208 extend outwardly from the proximal end portion 200a of the targeting cannula 200. These lugs 208 are configured to removably secure the targeting cannula 200 to the guide 1102.

Figure 14:
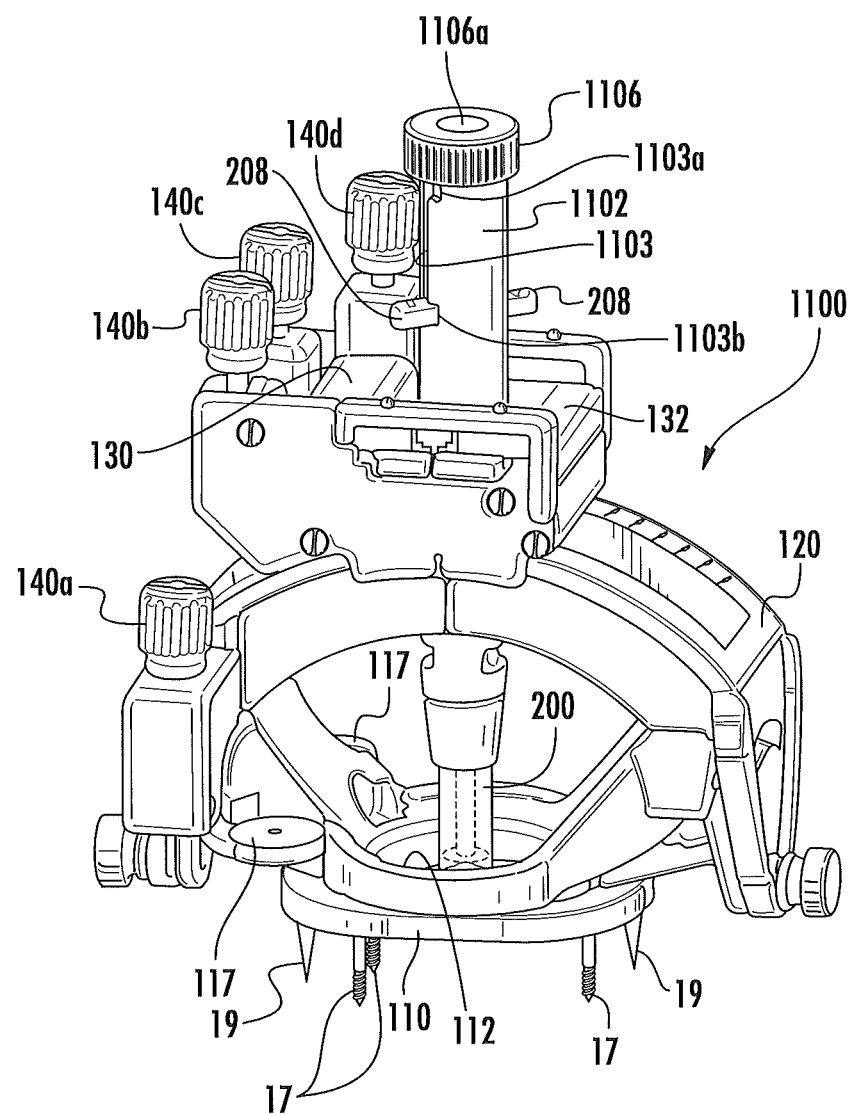
FIG. 14 illustrates the targeting cannula of FIG. 13 inserted within the guide and the cap removably secured to the guide proximal end portion.

The guide 1102 has opposite proximal and distal end portions 1102a, 1102b. In some embodiments, the proximal end portion 1102a contains threads 1104, as illustrated. These threads 1104 can be molded or machined into the guide 1102, as would be understood by those skilled in the art of the present invention. The threads 1104 are configured to threadingly engage a correspondingly threaded cap 1106 to secure a targeting cannula 200 and other devices within the guide 1102, and to allow for quick removal. FIG. 14 illustrates the targeting cannula 200 within the guide 1102 and the cap 1106 threadingly secured to the threads 1104 of the guide proximal end portion 1102a. The illustrated cap 1106 includes an opening 1106a to facilitate insertion of a probe or other device into and through the lumen 201 of the targeting cannula 200.

In other embodiments, the guide proximal end portion 1102a may include a detent (not shown) or similar structure formed therein and the cap 1106 may include a protrusion (not shown) configured to engage the detent so as to removably secure the cap 1106 and targeting cannula 200 to the guide 1102 (i.e., create a "snap fit") and to allow for quick removal. Alternatively, the guide proximal end portion 1102a may include a protrusion extending therefrom and the cap 1106 may include a detent formed therein that is configured to engage the protrusion so as to removably secure the cap and targeting cannula 200 to the guide 1102. In addition, various other ways of causing frictional engagement (e.g., an interference fit) may be utilized for removably securing the cap 1106 and targeting cannula 200 to the guide 1102 and to allow for quick removal, without limitation. Various shapes and/or components that allow for quick removal may be utilized, without limitation.

In some embodiments, the targeting cannula 200 and cap 1106 can be a preassembled unit.

The guide 1102 includes downwardly extending slots 1103, shown as a pair of opposing slots 1103, formed in the proximal end portion 1102a, thereof, as illustrated. Each slot 1103 includes an upper ledge portion 1103a and a lower ledge portion 1103b that are configured to engage the targeting cannula lugs 208. The lugs 208 cooperate with the slots 1103 to allow the targeting cannula 200 to be inserted within the guide 1102. By rotating the targeting cannula 200 such that the lugs 208 cooperate with the upper ledge portions 1103a, the targeting cannula 200 can be positioned at a first or upper position. By inserting the targeting cannula 200 further within the guide 1102 and then rotating the targeting cannula 200 such that the lugs 208 cooperate with the lower ledge portions 1103b, the targeting cannula 200 can be securely held at a second or lower position.

After the trajectory frame 1100 is aligned, a center punch (not shown) can be placed down the targeting cannula lumen 201 and pushed or tapped into the skull of a patient. This will create an incision in the scalp and provide a starting point for a drill bit. Alternately, an incision can be made in a patient's scalp first. In some instances, a center punch may not be required.

Figure 13:
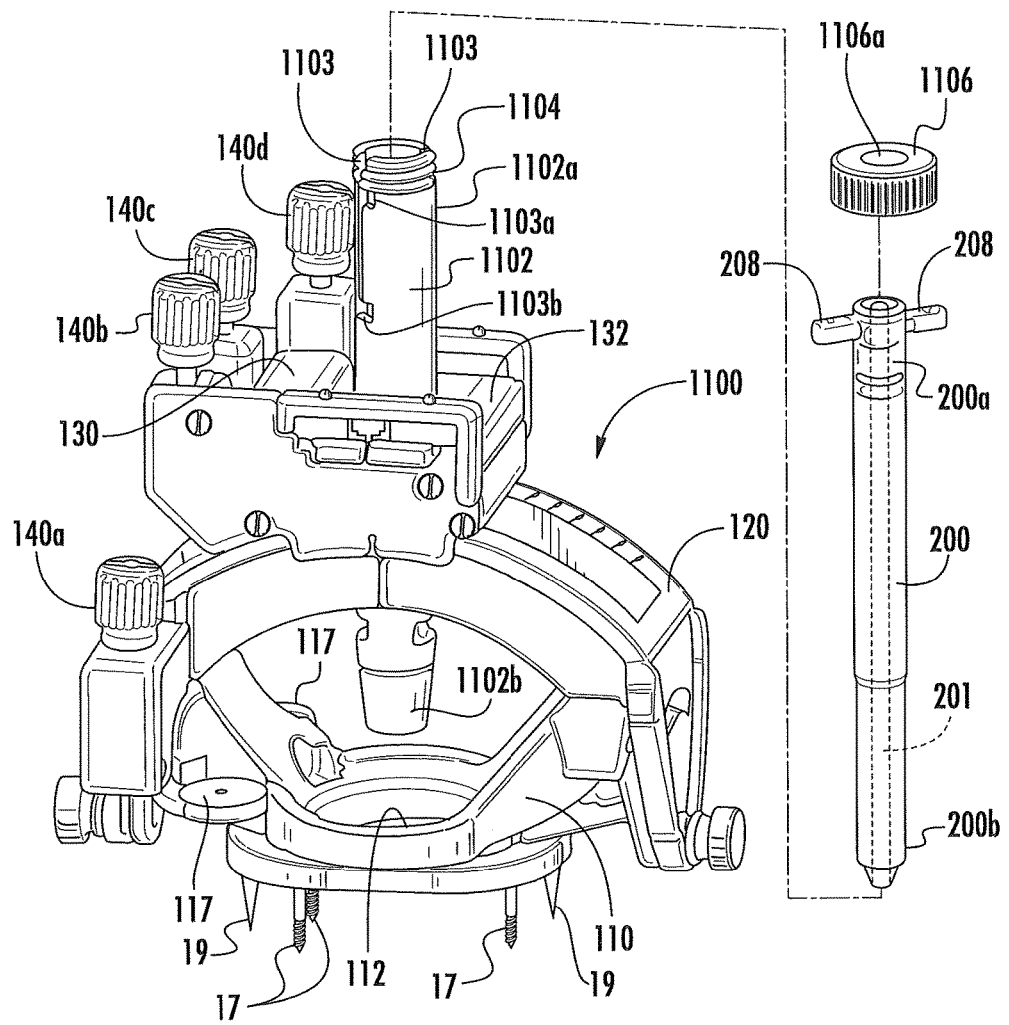
FIG. 13 is a partial exploded perspective view of a trajectory frame utilized in an MRI-guided interventional system, according to some embodiments of the present invention, wherein a guide includes a threaded proximal end portion for removably retaining a cap thereon that is configured to cover a targeting cannula and other devices inserted within the guide.
Figure 15A:
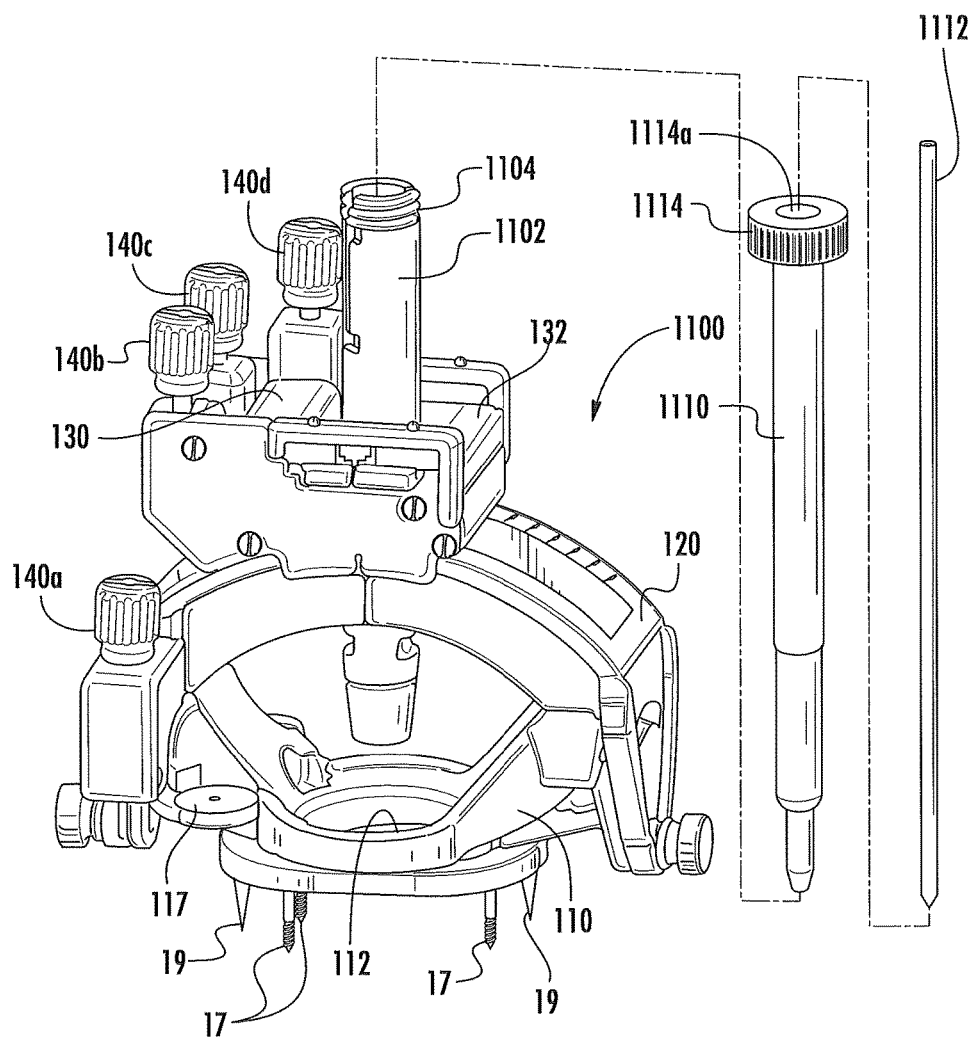
FIG. 15A is a partial exploded perspective view of a trajectory frame utilized in an MRI-guided interventional system, according to some embodiments of the present invention, wherein a guide includes a threaded proximal end portion for removably retaining a drill guide inserted within the guide.
Figure 15B:
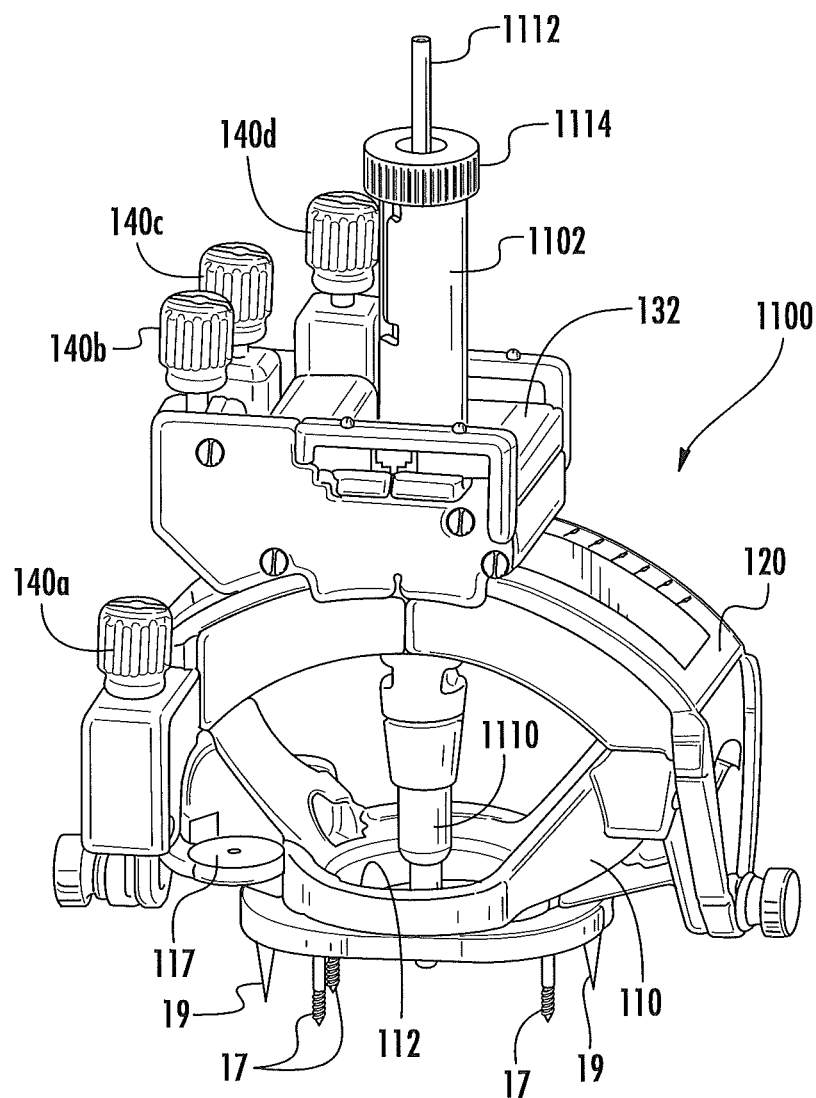
FIG. 15B illustrates the drill guide of FIG. 15A inserted within the guide and the threaded end of the drill guide threadingly secured to the threaded proximal end portion of the guide.

FIG. 15A illustrates the trajectory frame 1100 of FIG. 13 with the targeting cannula 200 removed from the guide 1102 and wherein the guide 1102 is configured to removably receive a drill guide 1110 and long drill bit 1112 inserted therewithin. FIG. 15B illustrates the drill guide 1110 of FIG. 15A inserted within the guide 1102 and a threaded cap 1114, having an opening 1114a, of the drill guide threadingly secured to the threads 1104 at the proximal end portion 1102a of the guide 1102. Alternatively, the cap 1114 of the drill guide may be attached to the guide proximal end 1102a via a detent or other similar structure, as described above. Once a hole is drilled in the skull of a patient via the drill bit 1112, the drill bit 1112 and drill guide 1110 are removed. Note that a drill guide 1110 and drill bit 1112 may not be required if an access (burr) hole is already made within the skull.

Figure 16A:
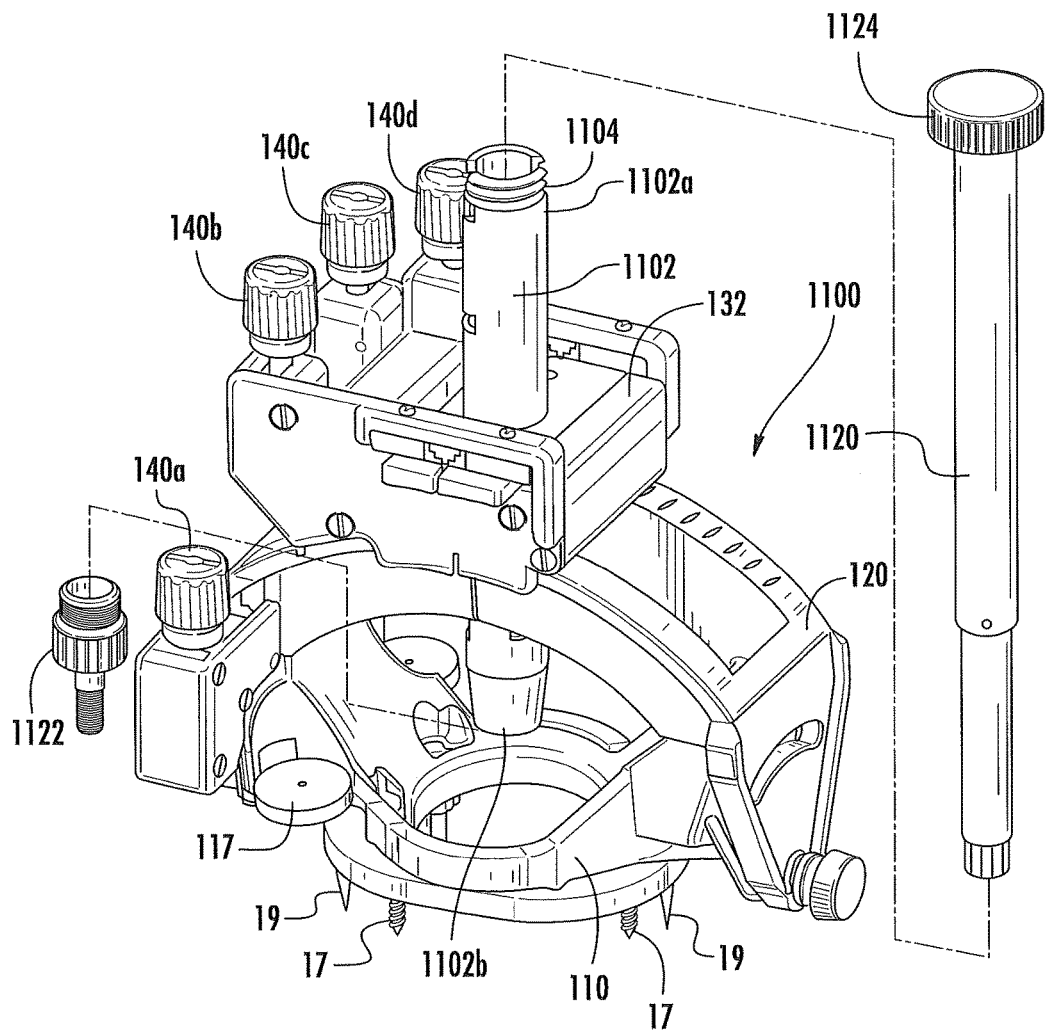
FIG. 16A is a partial exploded perspective view of a trajectory frame utilized in an MRI-guided interventional system, according to some embodiments of the present invention, and configured to removably receive a skull fixation device driver within the guide and a skull fixation device at the guide distal end.
Figure 16B:
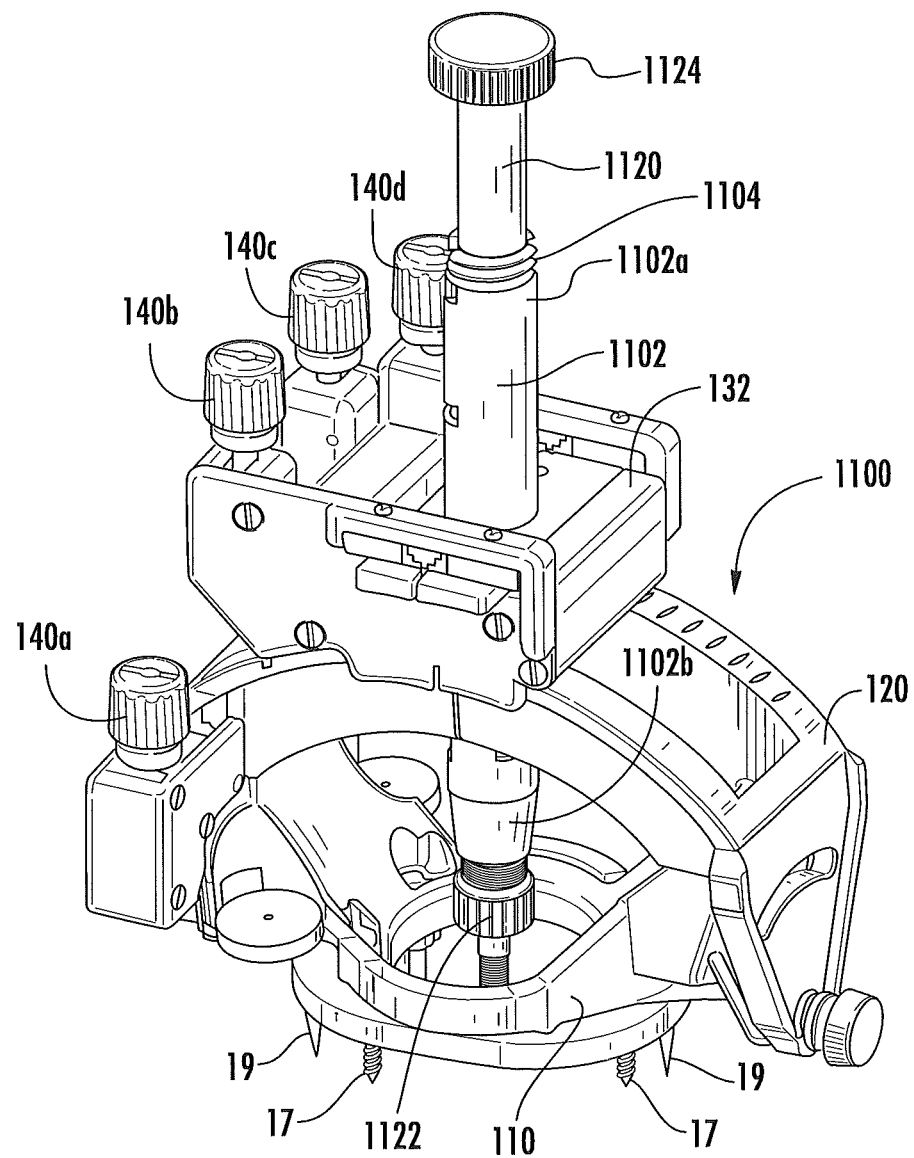
FIG. 16B illustrates the skull fixation device driver inserted within the guide via the proximal end portion thereof and the skull fixation device removably secured to the guide distal end.
Figure 17:
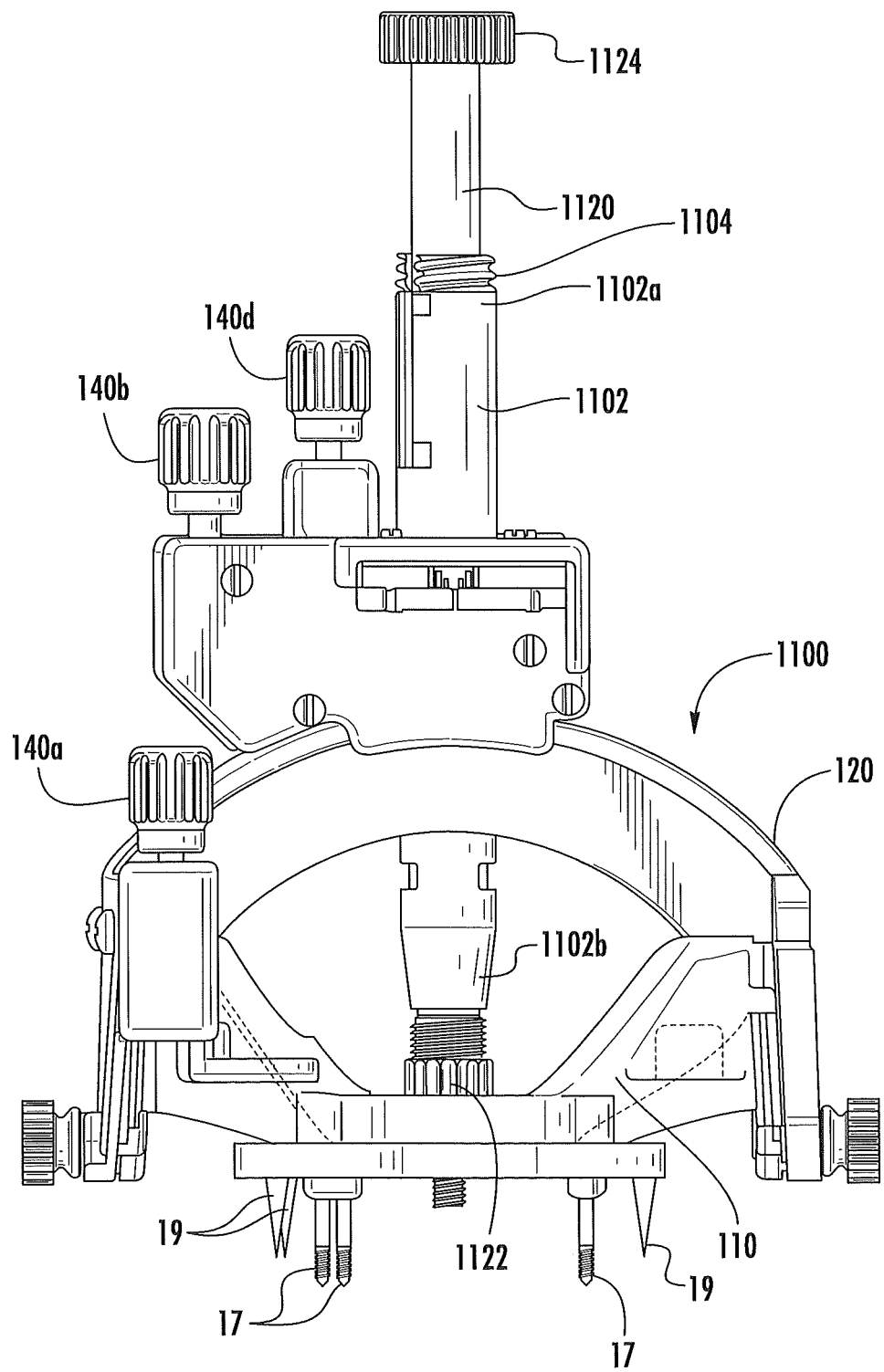
FIG. 17 is a side view of the trajectory frame of FIG. 16B.

FIGS. 16A-16B and 17 illustrate the trajectory frame 1100 of FIG. 13 with the targeting cannula 200 removed from the guide 1102 and wherein the guide 1102 is configured to removably receive a skull fixation device driver 1120 inserted through the proximal end portion 1102a thereof. A skull fixation device 1122 is inserted in the guide distal end 1102b. The skull fixation device 1122 and the skull fixation device driver 1120 are configured to be engaged such that the skull fixation device 1122 can be screwed into the skull of a patient by rotating and advancing the skull fixation device driver 1120 from the proximal end 1102a of the guide 1102. The illustrated skull fixation device driver 1120 is provided with a knob or handle 1124 that facilitates rotation of the skull fixation device driver 1120 by hand.

Figure 18A:
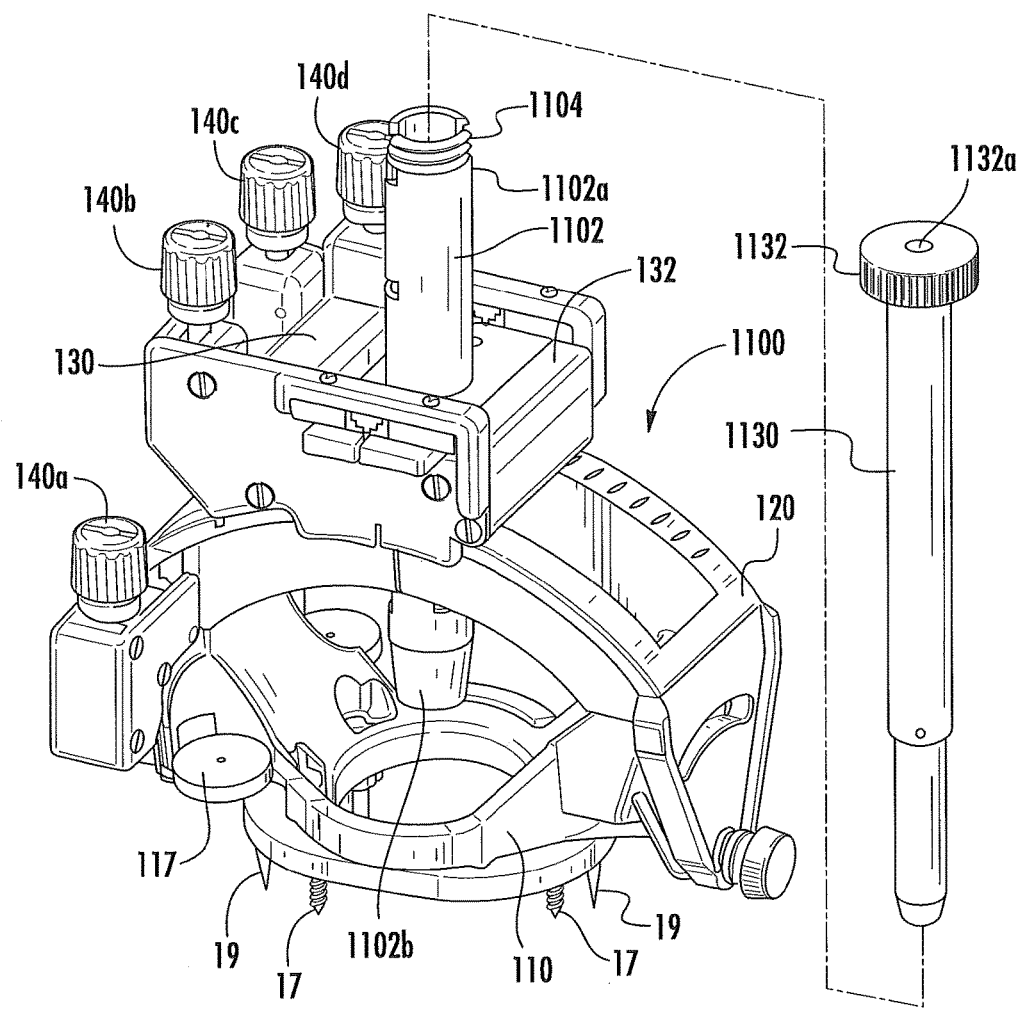
FIG. 18A is a partial exploded perspective view of a trajectory frame utilized in an MRI-guided interventional system, according to some embodiments of the present invention, and configured to removably receive a catheter guide within the guide.
Figure 18B:
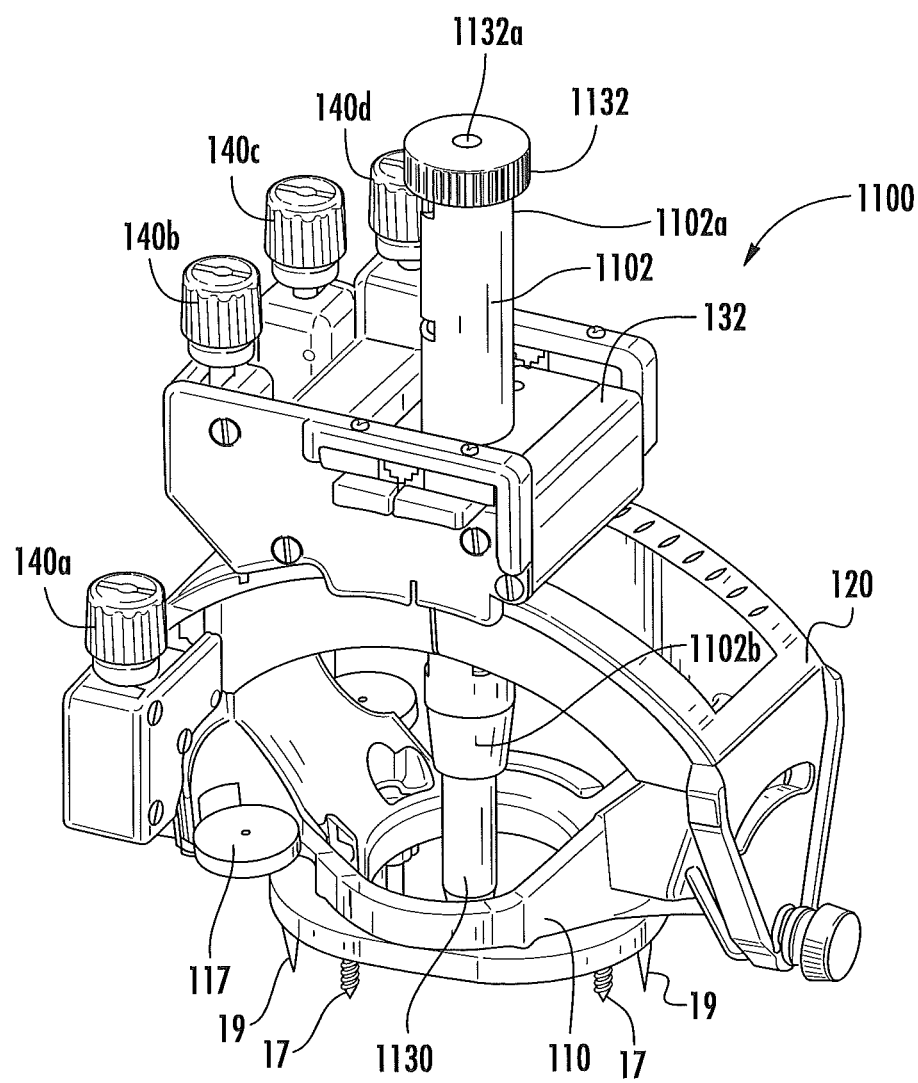
FIG. 18B is a perspective view of the trajectory frame of FIG. 18A and illustrating the catheter guide inserted within the guide and with a cap of the catheter guide secured to the proximal end portion of the guide.

As shown in FIGS. 18A-18B, after the skull fixation device 1122 is attached to the skull of a patient, the skull fixation device driver 1120 is removed from the guide 1102 and a catheter guide 1130 may be inserted within the guide 1102 through the proximal end 1102a thereof. The catheter guide 1130 includes a cap 1132 secured to a proximal end 1130a thereof that is threaded and configured to be threadingly secured to the threaded proximal end portion 1102a of the guide 1102. Alternatively, the cap 1132 of the catheter guide 1130 may be attached to the guide proximal end 1102a via a detent, interference fit, or via various other types of frictional engagement, and via various shapes and/or components that allow for quick removal, without limitation.

Figure 19:
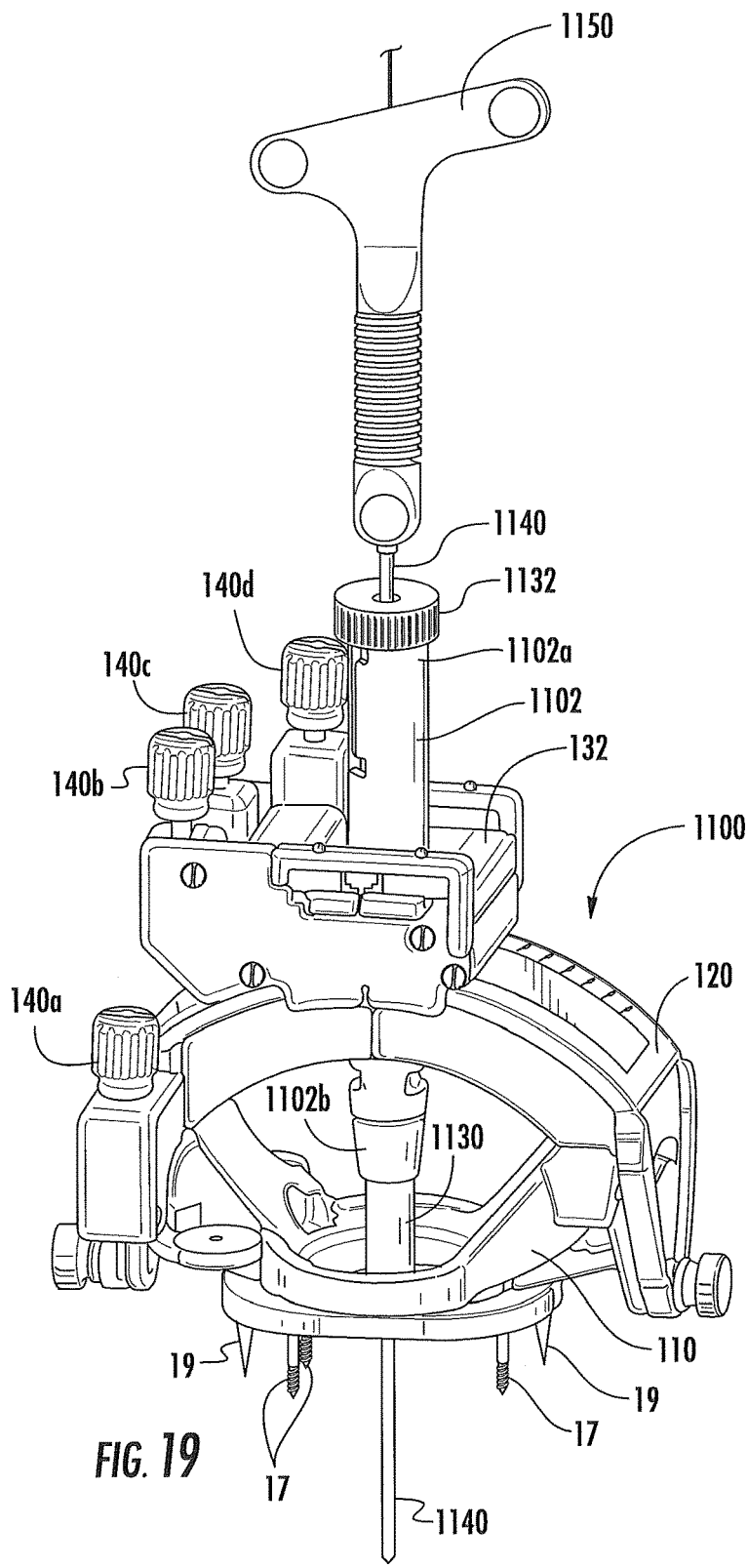
FIG. 19 is a perspective view of the trajectory frame of FIG. 18B and illustrating a catheter or other device advanced through the catheter guide of FIG. 18B.

The illustrated cap 1132 includes an opening 1132a to facilitate insertion of a probe or other device into and through the lumen 201 of the targeting cannula 200. FIG. 19 illustrates a catheter 1140 or other device advanced through the catheter guide 1130 via a tool 1150.

Figure 20A:
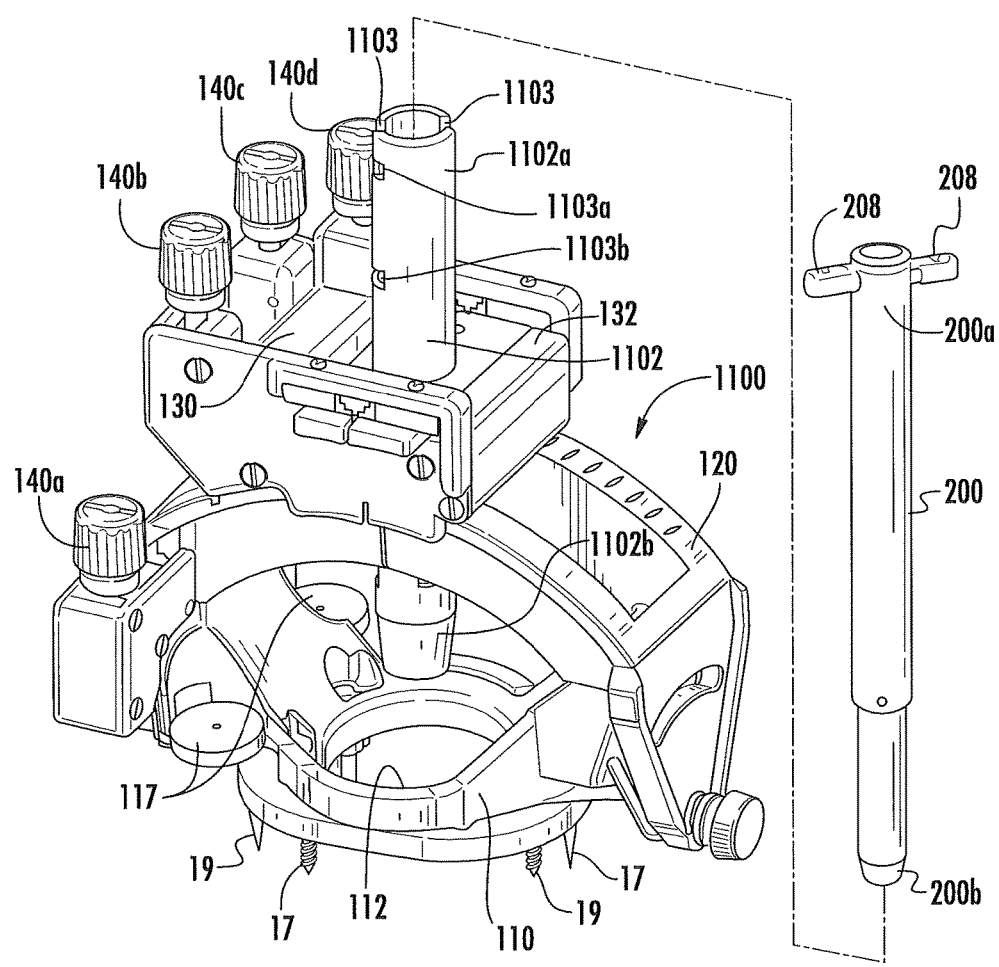
FIG. 20A is a partial exploded perspective view of a trajectory frame utilized in an MRI-guided interventional system, according to some embodiments of the present invention, wherein the trajectory frame includes a guide for removably receiving and securing targeting cannula therewithin.
Figure 20B:
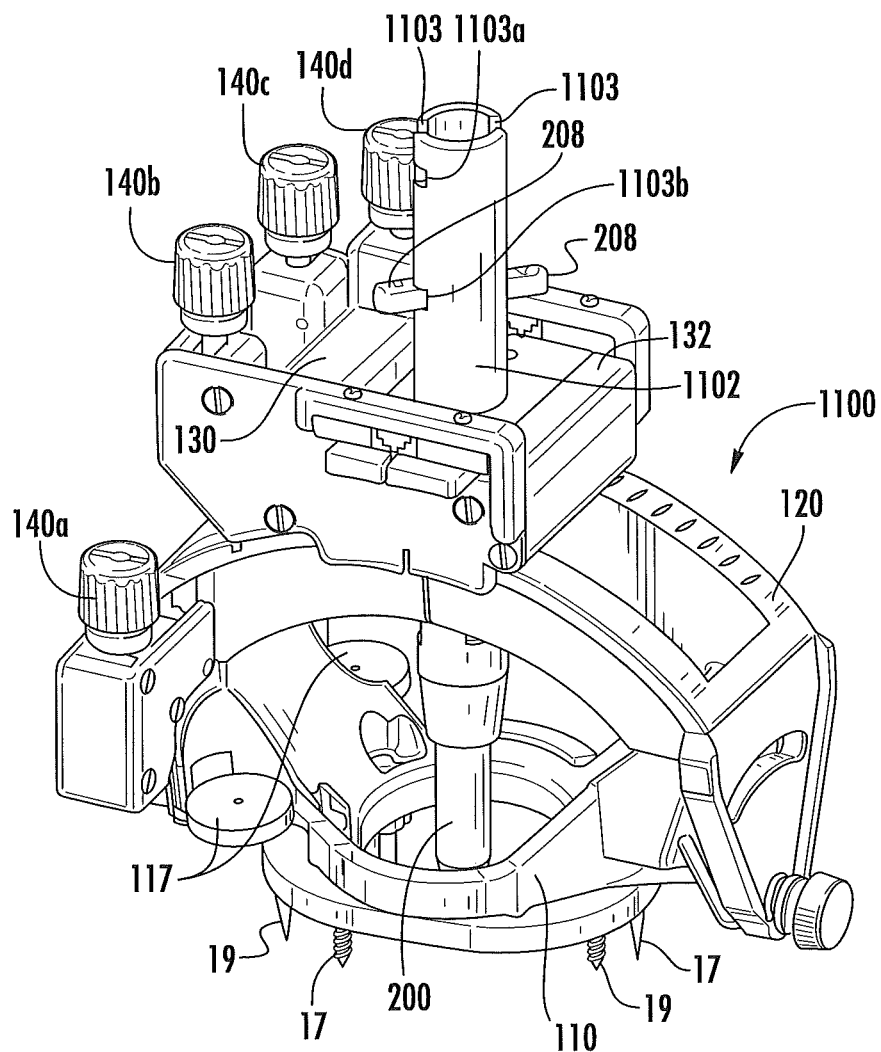
FIG. 20B illustrates the targeting cannula of FIG. 20A inserted within and secured to the guide.

Referring now to FIGS. 20A-20B, a trajectory frame 1100, according to other embodiments of the present invention, is illustrated. The trajectory frame 1100 is similar to the trajectory frame 1100 described above with respect to FIGS. 13-19, with the exception that the guide 1102 does not include a threaded proximal end portion 1102a. Various devices inserted within the guide 1102, such as the illustrated targeting cannula 200, are removably secured to the guide via lugs, such as targeting cannula lugs 208, that cooperate with elongated slots 1103 in the guide 1102. The elongated slots 1103 merge into spaced-apart transversely extending upper ledge portions (e.g., slots) 1103a and transversely extending lower ledge portions (e.g., slots) 1103b. The distance between the upper ledge portions 1103a and the lower edge portions 1103b is typically between about 0.25 inches and about 5.0 inches.

By rotating a device within the guide 1102 such that the lugs, for example the targeting cannula lugs 208, cooperate with the upper ledge portions 1103a, a device can be securely held at a first or upper position. By inserting the device further within the guide 1102 and then rotating the device such that the lugs cooperate with the lower ledge portions 1103*a*, the device can be securely held at a second or lower position.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A trajectory frame for use with an MRI-guided interventional system, comprising:
    a base having a patient access aperture formed therein, wherein the base is configured to be secured to the body of a patient;
    a yoke movably mounted to the base and rotatable about a roll axis;
    a platform movably mounted to the yoke and rotatable about a pitch axis;
    an elongated guide support secured to the platform, wherein the guide support comprises opposite proximal and distal end portions, wherein the guide support distal end portion is positioned proximate the patient access aperture, wherein the guide support comprises a bore therethrough that extends from the proximal end portion to the distal end portion; and
    a first device guide and a second different device guide releasably and separately positionable within the bore of the guide support such that a respective distal end of each is positioned proximate the patient access aperture, wherein the first device guide, when separately positioned within the bore of the guide support, is removably secured directly to the guide support, and wherein the second device guide, when separately positioned within the bore of the guide support, is removably secured directly to the guide support;
    wherein a proximal end of the first device guide and/or the second device guide comprises a cap configured to be removably secured to the guide support proximal end portion, wherein the cap comprises an opening to facilitate insertion of a device therethrough.

2. The trajectory frame of claim 1, wherein one of the first and second device guides is a targeting cannula.

3. The trajectory frame of claim 1, wherein the first device guide comprises an axially extending open lumen having an internal diameter that is different from an internal diameter of an axially extending open lumen of the second device guide.

4. The trajectory frame of claim 1, wherein the cap is configured to be removably secured to the guide support proximal end portion via a snap fit.

5. The trajectory frame of claim 1, further comprising a plurality of user-activatable actuators operably connected to the frame that are configured to translate and rotate the frame relative to the body of the patient.

6. The trajectory frame of claim 1, wherein the base comprises a plurality of locations for attaching the base to a body of a patient via fasteners.

7. The trajectory frame of claim 1, wherein the base is configured to be secured to the skull of a patient about a burr hole formed therein, and wherein the bore of the guide support is configured to guide intra-brain placement of a device in vivo.

8. The trajectory frame of claim 6, wherein the yoke comprises a first pair of spaced apart arcuate arms, wherein the platform engages and moves along the first pair of arcuate arms when rotated about the pitch axis, wherein the base comprises a second pair of spaced apart arcuate arms, and wherein the yoke engages and moves along the second pair of arcuate arms when rotated about the roll axis.

9. The trajectory frame of claim 1, wherein the platform comprises an X-Y support table movably mounted to the platform that is configured to move in an X-direction and Y-direction relative to the platform, and wherein the guide support is secured to the X-Y support table.

10. An MRI-guided medical assembly, comprising:
    a trajectory frame, comprising:
        a base having a patient access aperture formed therein, wherein the base is configured to be secured to the body of a patient;
        a yoke movably mounted to the base and rotatable about a roll axis; and
        a platform movably mounted to the yoke and rotatable about a pitch axis; and
        an elongated guide support secured to the platform, wherein the guide support comprises opposite proximal and distal end portions, wherein the guide support distal end portion is positioned proximate the patient access aperture, wherein the guide support comprises a bore therethrough that extends from the proximal end portion to the distal end portion; and
    a targeting cannula and a drill guide releasably and serially inserted within the bore;
    wherein the targeting cannula comprises an axially extending open lumen having an internal diameter that is different from an internal diameter of an axially extending open lumen of the drill guide, wherein the targeting cannula and drill guide each comprise respective opposite proximal and distal end portions, wherein the respective distal end portions of the targeting cannula and drill guide are separately positionable within the bore proximate the patient access aperture, and wherein the respective proximal end portions of the targeting cannula and drill guide are removably and separately secured directly to the guide support proximal end portion for quick release therefrom; and
    wherein the proximal end portion of the drill guide comprises a cap configured to be removably secured to the guide support proximal end portion, wherein the cap comprises an opening to facilitate insertion of a device through the drill guide.

11. The assembly of claim 10, wherein the guide support proximal end portion comprises threads formed therein, and wherein the cap threadingly engages the guide support proximal end portion.

12. The assembly of claim 10, wherein the cap is configured to be removably secured to the guide support proximal end portion via a snap fit.

13. The assembly of claim 10, wherein the guide support proximal end portion comprises at least one slot, wherein the targeting cannula is removably and separately secured directly to the guide support via at least one member extending outwardly from the targeting cannula that cooperates with the at least one slot.

14. The assembly of claim 10, further comprising a plurality of user-activatable actuators operably connected to the frame that are configured to translate and rotate the frame relative to the body of the patient.

15. The assembly of claim 10, wherein the platform comprises an X-Y support table movably mounted to the platform that is configured to move in an X-direction and Y-direction relative to the platform, and wherein the guide is secured to the X-Y support table.

\* \* \* \* \*